United States Patent
Runguphan et al.

(10) Patent No.: US 10,370,686 B2
(45) Date of Patent: Aug. 6, 2019

(54) YEAST CELL MODIFIED TO OVERPRODUCE FATTY ACID AND FATTY ACID-DERIVED COMPOUNDS

(71) Applicant: The Regents of the University of California, Oakland, CA (US)

(72) Inventors: Weerawat Runguphan, Mueang (TH); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/005,719

(22) Filed: Jan. 25, 2016

(65) Prior Publication Data

US 2016/0215308 A1    Jul. 28, 2016

Related U.S. Application Data

(63) Continuation of application No. PCT/US2014/048293, filed on Jul. 25, 2014.

(60) Provisional application No. 61/858,577, filed on Jul. 25, 2013.

(51) Int. Cl.
*C12P 7/64* (2006.01)
*C12N 1/19* (2006.01)
*C12N 9/10* (2006.01)
*C12N 9/00* (2006.01)
(Continued)

(52) U.S. Cl.
CPC .......... *C12P 7/6409* (2013.01); *C12N 9/1029* (2013.01); *C12N 9/93* (2013.01); *C12N 15/81* (2013.01); *C12P 7/04* (2013.01); *C12P 7/649* (2013.01); *C12P 7/6463* (2013.01); *C12Y 203/01085* (2013.01); *C12Y 604/01002* (2013.01); *Y02E 50/13* (2013.01)

(58) Field of Classification Search
CPC .......... C12P 7/64; C12P 7/6409; C12P 7/6436; C12P 7/649
See application file for complete search history.

(56) References Cited

U.S. PATENT DOCUMENTS

| | | | |
|---|---|---|---|
| 2012/0142979 A1 | 6/2012 | Keasling et al. | |
| 2013/0137149 A1* | 5/2013 | Phadnavis | C12N 15/815 435/134 |
| 2013/0197248 A1* | 8/2013 | Nielsen | C12N 9/1029 554/1 |

FOREIGN PATENT DOCUMENTS

| WO | WO2011157848 A1 | 12/2011 |
|---|---|---|
| WO | WO2012017083 A1 | 2/2012 |

OTHER PUBLICATIONS

International Search Report—Written Opinion for PCT/US2014/048293, dated Apr. 6, 2015.

(Continued)

*Primary Examiner* — Rebecca E Prouty
(74) *Attorney, Agent, or Firm* — Robin C. Chiang; Lawrence Berkeley National Laboratory

(57) ABSTRACT

The present invention provides for a genetically modified yeast host cell capable of producing one or more fatty acids, or fatty acid-derived compounds, or a mixture thereof, comprising: (a) increased expression of acetyl-CoA carboxylase (such as ACC1), (b) increased expression of one or more fatty acid synthases (such as FAS1 and FAS2), and (c) optionally reduced expression of one or more enzymes involved in or in the β-oxidation pathway (such as peroxisomal transporters PXA1 and PXA2, and β-oxidation enzymes POX1, POX2, and POX3).

11 Claims, 15 Drawing Sheets

Specification includes a Sequence Listing.

(51) Int. Cl.
    C12P 7/04     (2006.01)
    C12N 15/81    (2006.01)

(56) References Cited

OTHER PUBLICATIONS

International Preliminary Report on Patentability for PCT/US2014/048293, dated Jan. 26, 2016.
Al-Feel, W., Chirala, S. S., Wakil, S. J., 1992. Cloning of the yeast FAS3 gene and primary structure of yeast acetyl-CoA carboxylase. Proc Natl Acad Sci U S A. 89, 4534-8.
Bouvier-Nave, P., Benveniste, P., Oelkers, P., Sturley, S. L., Schaller, H., 2000. Expression in yeast and tobacco of plant cDNAs encoding acyl CoA:diacylglycerol acyltransferase. European journal of biochemistry / FEBS. 267, 85-96.
Cheng, J. B., Russell, D. W., 2004. Mammalian wax biosynthesis. I. Identification of two fatty acyl-Coenzyme A reductases with different substrate specificities and tissue distributions. The Journal of biological chemistry. 279, 37789-97.
Dahlqvist, A., Stahl, U., Lenman, M., Banas, A., Lee, M., Sandager, L., Ronne, H., Stymne, S., 2000. Phospholipid: diacylglycerol acyltransferase: an enzyme that catalyzes the acyl-CoAindependent formation of triacylglycerol in yeast and plants. Proc Natl Acad Sci U S A. 97, 6487-92.
Davis, M. S., Solbiati, J., Cronan, J. E., Jr., 2000. Overproduction of acetyl-CoA carboxylase activity increases the rate of fatty acid biosynthesis in *Escherichia coli*. The Journal of biological chemistry. 275, 28593-8.
Dmochowska, A., Dignard, D., Maleszka, R., Thomas, D. Y., 1990. Structure and transcriptional control of the *Saccharomyces cerevisiae* POX1 gene encoding acyl-coenzyme A oxidase. Gene. 88, 247-52.
Doan, T. T., Carlsson, A. S., Hamberg, M., Bulow, L., Stymne, S., Olsson, P., 2009. Functional expression of five *Arabidopsis* fatty acyl-CoA reductase genes in *Escherichia coli*. Journal of plant physiology. 166, 787-96.
Einerhand, A. W., Voorn-Brouwer, T. M., Erdmann, R., Kunau, W. H., Tabak, H. F., 1991. Regulation of transcription of the gene coding for peroxisomal 3-oxoacyl-CoA thiolase of *Saccharomyces cerevisiae*. European journal of biochemistry / FEBS. 200, 113-22.
Gupta, S., Dynamics of the Global Fatty Alcohol Market. 2004.
Hiltunen, J. K., Wenzel, B., Beyer, A., Erdmann, R., Fossa, A., Kunau, W. H., 1992. Peroxisomal multifunctional beta-oxidation protein of *Saccharomyces cerevisiae*. Molecular analysis of the fox2 gene and gene product. The Journal of biological chemistry. 267, 6646-53.
Hobbs, D. H., Lu, C., Hills, M. J., 1999. Cloning of a cDNA encoding diacylglycerol acyltransferase from *Arabidopsis thaliana* and its functional expression. FEBS letters. 452, 145-9.
Jako, C., Kumar, A., Wei, Y., Zou, J., Barton, D. L., Giblin, E. M., Covello, P. S., Taylor, D. C., 2001. Seed-specific over-expression of an *Arabidopsis* cDNA encoding a diacylglycerol acyltransferase enhances seed oil content and seed weight. Plant physiology. 126, 861-74.
Kalscheuer, R., Luftmann, H., Steinbuchel, A., 2004. Synthesis of novel lipids in *Saccharomyces cerevisiae* by heterologous expression of an unspecific bacterial acyltransferase. Applied and environmental microbiology. 70, 7119-25.
Kamisaka, Y., Tomita, N., Kimura, K., Kainou, K, Uemura, H., 2007. DGA1 (diacylglycerol acyltransferase gene) overexpression and leucine biosynthesis significantly increase lipid accumulation in the Deltasnf2 disruptant of *Saccharomyces cerevisiae*. The Biochemical journal. 408, 61-8.
Knoll, L. J., Johnson, D. R., Gordon, J. I., 1995. Complementation of *Saccharomyces cerevisiae* strains containing fatty acid activation gene (FAA) deletions with a mammalian acyl-CoA synthetase. The Journal of biological chemistry. 270, 10861-7.
Knudsen, J., Jensen, M. V., Hansen, J. K., Faergeman, N. J., Neergaard, T. B., Gaigg, B., 1999. Role of acylCoA binding protein in acylCoA transport, metabolism and cell signaling. Molecular and cellular biochemistry. 192, 95-103.
Liu, T., Vora, H., Khosla, C., 2010. Quantitative analysis and engineering of fatty acid biosynthesis in *E. coli*. Metab Eng. 12, 378-86.
Los, M., Czyz, A., Sell, E., Wegrzyn, A., Neubauer, P., Wegrzyn, G., 2004. Bacteriophage contamination: is there a simple method to reduce its deleterious effects in laboratory cultures and biotechnological factories? Journal of applied genetics. 45, 111-20.
Lu, X., Vora, H., Khosla, C., 2008. Overproduction of free fatty acids in *E. coli*: Implications for biodiesel production. Metab. Eng. 10, 333-339.
Metz, J. G., Pollard, M. R., Anderson, L., Hayes, T. R., Lassner, M. W., 2000. Purification of a jojoba embryo fatty acyl-coenzyme A reductase and expression of its cDNA in high erucic acid rapeseed. Plant physiology. 122, 635-44.
Moreira dos Santos, M., Raghevendran, V., Kotter, P., Olsson, L., Nielsen, J., 2004. Manipulation of malic enzyme in *Saccharomyces cerevisiae* for increasing NADPH production capacity aerobically in different cellular compartments. Metab Eng. 6, 352-63.
Nevoigt, E., Kohnke, J., Fischer, C. R., Alper, H., Stahl, U., Stephanopoulos, G., 2006. Engineering of promoter replacement cassettes for fine-tuning of gene expression in *Saccharomyces cerevisiae*. Applied and environmental microbiology. 72, 5266-73.
Ogiwara, H., Tanabe, T., Nikawa, J., Numa, S., 1978. Inhibition of rat-liver acetyl-coenzyme-A carboxylase by palmitoyl-coenzyme A. Formation of equimolar enzyme-inhibitor complex. European journal of biochemistry / FEBS. 89, 33-41.
Scharnewski, M., Pongdontri, R, Mora, G., Hoppert, M., Fulda, M., 2008. Mutants of *Saccharomyces cerevisiae* deficient in acyl-CoA synthetases secrete fatty acids due to interrupted fatty acid recycling. The FEBS journal. 275, 2765-78.
Schweizer, E., Hofmann, J., 2004. Microbial type I fatty acid synthases (FAS): major players in a network of cellular FAS systems. Microbiology and molecular biology reviews : MMBR. 68, 501-17.
Shani, N., Valle, D., 1996. A *Saccharomyces cerevisiae* homolog of the human adrenoleukodystrophy transporter is a heterodimer of two half ATP-binding cassette transporters. Proc Natl Acad Sci U S A. 93, 11901-6.
Shi, S., Valle-Rodriguez, J. O., Khoomrung, S., Siewers, V., Nielsen, J., 2012. Functional expression and characterization of five wax ester synthases in *Saccharomyces cerevisiae* and their utility for biodiesel production. Biotechnology for biofuels. 5, 7.
Steen, E. J., Kang, Y., Bokinsky, G., Hu, Z., Schirmer, A., McClure, A., del Cardayre, S. B., Keasling, J. D., 2010. Microbial production of fatty-acid-derived fuels and chemicals from plant biomass. Nature. 463, 559-562.
Stoveken, T., Kalscheuer, R., Malkus, U., Reichelt, R., Steinbuchel, A., 2005. The wax ester synthase/acyl coenzyme A:diacylglycerol acyltransferase from *Acinetobacter* sp. strain ADP1: characterization of a novel type of acyltransferase. Journal of bacteriology. 187, 1369-76.
Tai, M., Stephanopoulos, G., 2013. Engineering the push and pull of lipid biosynthesis in oleaginous yeast Yarrowia lipolytica for biofuel production. Metabolic engineering. 15, 1-9.
Trotter, P. J., 2001. The genetics of fatty acid metabolism in *Saccharomyces cerevisiae*. Annual review of nutrition. 21, 97-119.
US_Environmental_Protection_Agency, 2012 Renewable Fuel Standards. (website for: gpo.gov/fdsys/pkg/FR-2012-01-09/pdf/2011-33451.pdf).
Vioque, J., Kolattukudy, P. E., 1997. Resolution and purification of an aldehyde-generating and an alcohol-generating fatty acyl-CoA reductase from pea leaves (*Pisum sativum* L.). Archives of biochemistry and biophysics. 340, 64-72.
Westfall, P. J., Pitera, D. J., Lenihan, J. R., Eng, D., Woolard, F. X., Regentin, R., Horning, T., Tsuruta, H., Melis, D. J., Owens, A., Fickes, S., Diola, D., Benjamin, K. R., Keasling, J. D., Leavell, M. D., McPhee, D. J., Renninger, N. S., Newman, J. D., Paddon, C. J., 2012. Production of amorphadiene in yeast, and its conversion to dihydroartemisinic acid, precursor to the antimalarial agent artemisinin. Proceedings of the National Academy of Sciences of the United States of America. 109, E111-8.

(56) References Cited

OTHER PUBLICATIONS

Wynn, J. P., bin Abdul Hamid, A., Ratledge, C., 1999. The role of malic enzyme in the regulation of lipid accumulation in filamentous fungi. Microbiology. 145 ( Pt 8), 1911-7.

Yu, K. O., Jung, J., Kim, S. W., Park, C. H., Han, S. O., 2012. Synthesis of FAEEs from glycerol in engineered *Saccharomyces cerevisiae* using endogenously produced ethanol by heterologous expression of an unspecific bacterial acyltransferase. Biotechnology and bioengineering. 109, 110-5.

Zhang, Y., Adams, I. P., Ratledge, C., 2007. Malic enzyme: the controlling activity for lipid production? Overexpression of malic enzyme in Mucor circinelloides leads to a 2.5-fold increase in lipid accumulation. Microbiology. 153, 2013-25.

\* cited by examiner

SEQUENCE LISTING

```
<160> NUMBER OF SEQ ID NOS: 60

<210> SEQ ID NO 1
<211> LENGTH: 30
<212> TYPE: DNA
<213> ORGANISM: Saccharomyces cerevisiae

<400> SEQUENCE: 1
atatatacta gtatgaagcc ggaagttgag                                        30

<210> SEQ ID NO 2
<211> LENGTH: 33
<212> TYPE: DNA
<213> ORGANISM: Saccharomyces cerevisiae

<400> SEQUENCE: 2
atatatacta gtctatttct tagtagaaac ggc                                    33

<210> SEQ ID NO 3
<211> LENGTH: 40
<212> TYPE: DNA
<213> ORGANISM: Saccharomyces cerevisiae

<400> SEQUENCE: 3
atatatggat ccaaaacaat ggacgcttac tccacaagac                             40

<210> SEQ ID NO 4
<211> LENGTH: 34
<212> TYPE: DNA
<213> ORGANISM: Saccharomyces cerevisiae

<400> SEQUENCE: 4
ctccagttaa tttcggaacc cgccaaagcc ttaa                                   34

<210> SEQ ID NO 5
<211> LENGTH: 34
<212> TYPE: DNA
<213> ORGANISM: Saccharomyces cerevisiae

<400> SEQUENCE: 5
ttaaggcttt ggcgggttcc gaaattaact ggag                                   34

<210> SEQ ID NO 6
<211> LENGTH: 37
<212> TYPE: DNA
<213> ORGANISM: Saccharomyces cerevisiae

<400> SEQUENCE: 6
atatatctcg agttaggatt gttcatactt ttcccag                                37

<210> SEQ ID NO 7
<211> LENGTH: 35
<212> TYPE: DNA
<213> ORGANISM: Saccharomyces cerevisiae

<400> SEQUENCE: 7
atatatgcgg ccgcatgagc gaagaaagct tattc                                  35

<210> SEQ ID NO 8
```

```
<211> LENGTH: 35
<212> TYPE: DNA
<213> ORGANISM: Saccharomyces cerevisiae

<400> SEQUENCE: 8
atatatgcgg ccgcttattt caaagtcttc aacaa                         35

<210> SEQ ID NO 9
<211> LENGTH: 39
<212> TYPE: DNA
<213> ORGANISM: Saccharomyces cerevisiae

<400> SEQUENCE: 9
atatatggat ccaaaacaat gtcaggaaca ttcaatgat                     39

<210> SEQ ID NO 10
<211> LENGTH: 36
<212> TYPE: DNA
<213> ORGANISM: Saccharomyces cerevisiae

<400> SEQUENCE: 10
atatatgtcg acttacccaa ctatcttcaa ttctgc                        36

<210> SEQ ID NO 11
<211> LENGTH: 39
<212> TYPE: DNA
<213> ORGANISM: Escherichia coli

<400> SEQUENCE: 11
atatatacta gtaaaacaat ggcggacacg ttattgatt                     39

<210> SEQ ID NO 12
<211> LENGTH: 33
<212> TYPE: DNA
<213> ORGANISM: Escherichia coli

<400> SEQUENCE: 12
atatatagat ctttatgagt catgatttac taa                           33

<210> SEQ ID NO 13
<211> LENGTH: 36
<212> TYPE: DNA
<213> ORGANISM: Saccharomyces cerevisiae

<400> SEQUENCE: 13
atatatggat ccaaaacaat ggtgagcatc ccagag                        36

<210> SEQ ID NO 14
<211> LENGTH: 32
<212> TYPE: DNA
<213> ORGANISM: Saccharomyces cerevisiae

<400> SEQUENCE: 14
atatatgtcg acttagtagc gcatggtgga gg                            32

<210> SEQ ID NO 15
<211> LENGTH: 34
<212> TYPE: DNA
<213> ORGANISM: Saccharomyces cerevisiae

<400> SEQUENCE: 15
atatatacta gtaaacaatg gctttgtctt catt                          34
```

<210> SEQ ID NO 16
<211> LENGTH: 32
<212> TYPE: DNA
<213> ORGANISM: Saccharomyces cerevisiae

<400> SEQUENCE: 16
atatatagat ctttataagt gtggagcgaa ag                            32

<210> SEQ ID NO 17
<211> LENGTH: 26
<212> TYPE: DNA
<213> ORGANISM: Acinetobacter calcoaceticus

<400> SEQUENCE: 17
atatatggat ccaaaacaat gggtag                                   26

<210> SEQ ID NO 18
<211> LENGTH: 25
<212> TYPE: DNA
<213> ORGANISM: Acinetobacter calcoaceticus

<400> SEQUENCE: 18
atatatgtcg acttagtttg cggtt                                    25

<210> SEQ ID NO 19
<211> LENGTH: 64
<212> TYPE: DNA
<213> ORGANISM: Artificial Sequence
<220> FEATURE:
<223> OTHER INFORMATION: Primer with seqeunces homologous to plasmids
      p416Tef1 and pUG72

<400> SEQUENCE: 19
tacgccaagc gcgcaattaa ccctcactaa agggaacaaa agctgcagct gaagcttcgt    60
acgc                                                              64

<210> SEQ ID NO 20
<211> LENGTH: 66
<212> TYPE: DNA
<213> ORGANISM: Artificial Sequence
<220> FEATURE:
<223> OTHER INFORMATION: Primer with seqeunces homologous to plasmids
      p416Tef1 and pUG72

<400> SEQUENCE: 20
aaaatctgga agagtaaaaa aggagtagaa acattttgaa gctatgcata ggccactagt    60
ggatct                                                            66

<210> SEQ ID NO 21
<211> LENGTH: 60
<212> TYPE: DNA
<213> ORGANISM: Saccharomyces cerevisiae

<400> SEQUENCE: 21
cacaattgtt atcggttcta caattgttct gctctcttca atcagctgaa gcttcgtacg    60

<210> SEQ ID NO 22
<211> LENGTH: 60
<212> TYPE: DNA
<213> ORGANISM: Saccharomyces cerevisiae

<400> SEQUENCE: 22
catcttctgt ggagaagact cgaataagct ttcttcgctc attagttcta gaaaacttag    60

<210> SEQ ID NO 23
<211> LENGTH: 68
<212> TYPE: DNA
<213> ORGANISM: Saccharomyces cerevisiae

<400> SEQUENCE: 23
caccgaaaag tgttgaacga ttcactgcga caataatcag agattacagt cagctgaagc    60
ttcgtacg                                                              68

<210> SEQ ID NO 24
<211> LENGTH: 68
<212> TYPE: DNA
<213> ORGANISM: Saccharomyces cerevisiae

<400> SEQUENCE: 24
tctaaagaac cgtgagatag ggttaatggt cttgtggagt aagcgtccat tagttctaga    60
aaacttag                                                              68

<210> SEQ ID NO 25
<211> LENGTH: 68
<212> TYPE: DNA
<213> ORGANISM: Saccharomyces cerevisiae

<400> SEQUENCE: 25
ttactatatt tcctaaattt tctctggtct gcaggccaaa acaacaact cagctgaagc     60 ttcgtacg                                                              68

<210> SEQ ID NO 26
<211> LENGTH: 68
<212> TYPE: DNA
<213> ORGANISM: Saccharomyces cerevisiae

<400> SEQUENCE: 26
aattcagtta gcaaaatatg agctaattct tgctcaactt ccggcttcat tagttctaga    60
aaacttag                                                              68

<210> SEQ ID NO 27
<211> LENGTH: 71
<212> TYPE: DNA
<213> ORGANISM: Saccharomyces cerevisiae

<400> SEQUENCE: 27
tacaataaaa actagaacaa acacaaaaga caaaaaaga caacaatatg cataggccac     60
tagtggatct g                                                          71

<210> SEQ ID NO 28
<211> LENGTH: 70
<212> TYPE: DNA
<213> ORGANISM: Saccharomyces cerevisiae

<400> SEQUENCE: 28
agtgctttag tatgatgagg ctttcctatc atggaaatgt tgatccatta cagctgaagc    60
ttcgtacgct                                                            70

<210> SEQ ID NO 29
<211> LENGTH: 71
<212> TYPE: DNA
<213> ORGANISM: Saccharomyces cerevisiae

<400> SEQUENCE: 29

```
tctctgttct tcactatttc ttgaaaaact aagaagtacg catcaaaatg cataggccac    60
tagtggatct g                                                         71

<210> SEQ ID NO 30
<211> LENGTH: 70
<212> TYPE: DNA
<213> ORGANISM: Saccharomyces cerevisiae

<400> SEQUENCE: 30
tagtgtttat gaagggcagg ggggaaagta aaaactatg tcttccttta cagctgaagc     60
ttcgtacgct                                                           70

<210> SEQ ID NO 31
<211> LENGTH: 21
<212> TYPE: DNA
<213> ORGANISM: Saccharomyces cerevisiae

<400> SEQUENCE: 31 accccctcact tgtcgtgaga c                                             21

<210> SEQ ID NO 32
<211> LENGTH: 18
<212> TYPE: DNA
<213> ORGANISM: Saccharomyces cerevisiae

<400> SEQUENCE: 32
ttaatgggga gcgctgat                                                  18

<210> SEQ ID NO 33
<211> LENGTH: 22
<212> TYPE: DNA
<213> ORGANISM: Saccharomyces cerevisiae

<400> SEQUENCE: 33
gttgacataa aagcgagaat ac                                             22

<210> SEQ ID NO 34
<211> LENGTH: 18
<212> TYPE: DNA
<213> ORGANISM: Saccharomyces cerevisiae

<400> SEQUENCE: 34
ttaatgggga gcgctgat                                                  18

<210> SEQ ID NO 35
<211> LENGTH: 18
<212> TYPE: DNA
<213> ORGANISM: Saccharomyces cerevisiae

<400> SEQUENCE: 35
cagcatgtga aaaaccc                                                   18

<210> SEQ ID NO 36
<211> LENGTH: 18
<212> TYPE: DNA
<213> ORGANISM: Saccharomyces cerevisiae

<400> SEQUENCE: 36
ggcagtaact acgtagtg                                                  18

<210> SEQ ID NO 37
```

```
<211> LENGTH: 18
<212> TYPE: DNA
<213> ORGANISM: Saccharomyces cerevisiae

<400> SEQUENCE: 37
cttactcaat tgtttaat                                                 18

<210> SEQ ID NO 38
<211> LENGTH: 18
<212> TYPE: DNA
<213> ORGANISM: Saccharomyces cerevisiae

<400> SEQUENCE: 38
gcgagtttgt aagtattt                                                 18

<210> SEQ ID NO 39
<211> LENGTH: 18
<212> TYPE: DNA
<213> ORGANISM: Saccharomyces cerevisiae

<400> SEQUENCE: 39
aagaacaaga acaacaaa                                                 18

<210> SEQ ID NO 40
<211> LENGTH: 18
<212> TYPE: DNA
<213> ORGANISM: Saccharomyces cerevisiae

<400> SEQUENCE: 40
tgccttaatc atgacagg                                                 18

<210> SEQ ID NO 41
<211> LENGTH: 19
<212> TYPE: DNA
<213> ORGANISM: Saccharomyces cerevisiae

<400> SEQUENCE: 41
cctcccattg atatttaag                                                19

<210> SEQ ID NO 42
<211> LENGTH: 18
<212> TYPE: DNA
<213> ORGANISM: Saccharomyces cerevisiae

<400> SEQUENCE: 42
tagttctaga aaacttag                                                 18

<210> SEQ ID NO 43
<211> LENGTH: 18
<212> TYPE: DNA
<213> ORGANISM: Saccharomyces cerevisiae

<400> SEQUENCE: 43
cccatcgcat atcaggag                                                 18

<210> SEQ ID NO 44
<211> LENGTH: 21
<212> TYPE: DNA
<213> ORGANISM: Saccharomyces cerevisiae

<400> SEQUENCE: 44
ggtaatgctt cttatgtgag g                                             21
```

```
<210> SEQ ID NO 45
<211> LENGTH: 19
<212> TYPE: DNA
<213> ORGANISM: Saccharomyces cerevisiae

<400> SEQUENCE: 45
ttaccccaac aaaaacagc                                          19

<210> SEQ ID NO 46
<211> LENGTH: 21
<212> TYPE: DNA
<213> ORGANISM: Saccharomyces cerevisiae

<400> SEQUENCE: 46
ataatgtcaa tcttgtcttg c                                       21

<210> SEQ ID NO 47
<211> LENGTH: 20
<212> TYPE: DNA
<213> ORGANISM: Saccharomyces cerevisiae

<400> SEQUENCE: 47
gcgagagcta ggcagctatt                                         20

<210> SEQ ID NO 48
<211> LENGTH: 20
<212> TYPE: DNA
<213> ORGANISM: Saccharomyces cerevisiae

<400> SEQUENCE: 48
atcgttcacc gtcagaacaa                                         20

<210> SEQ ID NO 49
<211> LENGTH: 20
<212> TYPE: DNA
<213> ORGANISM: Saccharomyces cerevisiae

<400> SEQUENCE: 49
atattcggtt ctggtttcgg                                         20

<210> SEQ ID NO 50
<211> LENGTH: 20
<212> TYPE: DNA
<213> ORGANISM: Saccharomyces cerevisiae

<400> SEQUENCE: 50
ccctcgaacc aaataggaaa                                         20

<210> SEQ ID NO 51
<211> LENGTH: 20
<212> TYPE: DNA
<213> ORGANISM: Saccharomyces cerevisiae

<400> SEQUENCE: 51
gccagaacaa gatgggaaat                                         20

<210> SEQ ID NO 52
<211> LENGTH: 20
<212> TYPE: DNA
<213> ORGANISM: Saccharomyces cerevisiae

<400> SEQUENCE: 52
tgtatggacg acccttcaaa                                         20
```

<210> SEQ ID NO 53
<211> LENGTH: 20
<212> TYPE: DNA
<213> ORGANISM: Saccharomyces cerevisiae

<400> SEQUENCE: 53
gggttacttc tccgtgggta                                           20

<210> SEQ ID NO 54
<211> LENGTH: 20
<212> TYPE: DNA
<213> ORGANISM: Saccharomyces cerevisiae

<400> SEQUENCE: 54
aattccttca gggcaacaac                                           20

<210> SEQ ID NO 55
<211> LENGTH: 20
<212> TYPE: DNA
<213> ORGANISM: Saccharomyces cerevisiae

<400> SEQUENCE: 55
aacatgcaac gtctccacat                                           20

<210> SEQ ID NO 56
<211> LENGTH: 20
<212> TYPE: DNA
<213> ORGANISM: Saccharomyces cerevisiae

<400> SEQUENCE: 56
tggagaacca ccgtttaaca                                           20

<210> SEQ ID NO 57
<211> LENGTH: 20
<212> TYPE: DNA
<213> ORGANISM: Saccharomyces cerevisiae

<400> SEQUENCE: 57
tgctcattgg atatgggcta                                           20

<210> SEQ ID NO 58
<211> LENGTH: 20
<212> TYPE: DNA
<213> ORGANISM: Saccharomyces cerevisiae

<400> SEQUENCE: 58
tagttccgac aaggtcacca                                           20

<210> SEQ ID NO 59
<211> LENGTH: 20
<212> TYPE: DNA
<213> ORGANISM: Saccharomyces cerevisiae

<400> SEQUENCE: 59
ttaccatcca cacggcatag                                           20

<210> SEQ ID NO 60
<211> LENGTH: 24

```
<212> TYPE: DNA
<213> ORGANISM: Saccharomyces cerevisiae

<400> SEQUENCE: 60
tgaccagtgt catcagagaa atag                                              24
```

YEAST CELL MODIFIED TO OVERPRODUCE FATTY ACID AND FATTY ACID-DERIVED COMPOUNDS

CROSS-REFERENCE TO RELATED APPLICATIONS

This application claims priority as a continuation application to PCT International Patent Application No. PCT/US14/48293, filed Jul. 25, 2014, which claims priority to U.S. Provisional Patent Application Ser. No. 61/858,577, filed Jul. 25, 2013, which are hereby both incorporated by reference in their entireties.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of production of fatty acid, or fatty acid-derived compounds, and in particular host cells that are genetically modified to produce fatty acid, or fatty acid-derived compounds.

BACKGROUND OF THE INVENTION

Unsustainable demands, rising oil costs and concerns over climate change have inspired interest in renewable fuels and chemicals (Fortman et al., 2008). Microbial production of high-energy fuels via economically efficient and environmentally sustainable bioprocesses has recently emerged as a viable alternative to the conventional production of transportation fuels (Lynd et al., 2005). Fatty acids, sometimes touted as nature's 'petroleum', are long-chain carboxylic acids that cells use for both chemical and energy storage functions. These energy-rich molecules are currently derived from plant oils and animal fats. However, increasing food prices worldwide have rekindled debate over the competition of agricultural resources between the energy sector and the food industry. Therefore, alternatives to agricultural crops are urgently needed for the production of sustainable and economical biofuels. Namely, producing fatty acid-derived biofuels directly from abundant and cost-effective renewable resources by microbial fermentation is an attractive alternative biofuel production method.

In the phospholipid form, fatty acids are a major component of cell membranes in all organisms. Certain species of yeasts and microalgae can accumulate fatty acids in the neutral form as triacylglycerols (TAG) at up to 30-70% of dry cell weight (Beopoulos et al., 2009). While naturally possessing a lower lipid content (between 3.5 and 10.7% of DCW) (Johnson et al., 1972), S. cerevisiae offers several advantages over oleaginous yeasts and microalgae as a production host for fatty acids and derivatives. Namely, S. cerevisiae is more genetically tractable than oleaginous yeasts and microalgae; thus, genetic tools for metabolic pathway manipulation are more abundant. Second, the generation, isolation, and analysis of S. cerevisiae mutant strains can be performed with relative ease, and deletion strains for most coding genes are commercially available. Third, S. cerevisiae has a proven track record in various industrial applications, and the fermentation of S. cerevisiae has been previously manipulated to produce numerous heterologous metabolites. Finally, S. cerevisiae is easily cultivated in chemically defined medium and exhibits fast growth rates, thus facilitating scaling-up processes.

Because fatty acids are integral parts of all living organisms, their biosynthesis and regulation have been comprehensively studied in both prokaryotes and eukaryotes (Magnuson et al., 1993; Tehlivets et al., 2007). In the yeast S. cerevisiae, fatty acid biosynthesis serves many important functions including energy metabolism, posttranslational protein modifications and membrane lipid biosynthesis. De novo fatty acid biosynthesis in S. cerevisiae requires acetyl-CoA carboxylase (ACC; encoded by the ACC1 gene) and the fatty acid synthase complex (FAS; encoded by FAS1 and FAS2) (Al-Feel et al., 1992) (FIG. 1). ACC converts acetyl-CoA into malonyl-CoA. Subsequently, the FAS complex condenses one equivalent of acetyl-CoA and 7-8 equivalents of malonyl-CoA into C16-C18 fatty acyl-CoAs. Yeast FAS complex is a 2.6-MDa protein consisting of two non-identical, multifunctional subunits, α and β, organized as a hexamer ($\alpha_6\beta_6$) (Schweizer and Hofmann, 2004). The α subunit, encoded by FAS2, contains β-ketoacyl synthase (KS), β-ketoacyl reductase (KR), and acyl carrier protein (ACP) domains. The β subunit, encoded by FAS1, contains acetyl-, malonyl-, and palmitoyl-transferase (AT and MPT), as well as dehydratase (DH) and enoyl reductase (ER) domains. As they emerge from the FAS complex, newly synthesized fatty-acyl CoAs are bound to acyl-CoA binding protein (ACBP; encoded by the ACBP1 gene), which facilitates intracellular transport of acyl-CoA to the endoplasmic reticulum and lipid bodies for phospholipids and TAG biosynthesis (Knudsen et al., 1999). Notably, all of S. cerevisiae C16-C18 fatty acid biosynthesis enzymes are encoded by merely two genes (FAS1 and FAS2), as opposed to ten separate genes (FabA, FabB, FabD, FabF, FabG, FabH, FabI, FabZ, Acp and TesA) as is the case for E. coli. This distinction allows us to overexpress the entire pathway in a more straightforward manner.

Because fatty acids serve multiple cellular functions in yeast, their biosynthesis—from the conversion of acetyl-CoA to malonyl-CoA by ACC to the subsequent production of fatty acyl-CoA by the FAS complex—is tightly regulated at multiple levels (Tehlivets et al., 2007). Moreover, fatty acid biosynthesis is feedback inhibited by long chain acyl-CoA. ACC is inhibited by extremely low concentrations of long-chain acyl-CoA, ($K_i$=1-5 nM) (Ogiwara et al., 1978). Altogether, these mechanisms ensure that the cell does not accumulate excess quantities of this energy-rich metabolite. In order to overproduce fatty acid-derived biofuels in S. cerevisiae, these regulatory elements must be mitigated. A common strategy to relieve feedback inhibition by acyl-CoA is the overexpression of either the endogenous or heterologous acyl-acyl carrier protein (ACP) or acyl-CoA thioesterase to produce free fatty acids (FIG. 1).

While TAGs and free fatty acids are valuable, they cannot be used directly as fuels and must first be chemically processed prior to utilization. Therefore, renewable fuels that are directly compatible with existing infrastructure are in great demand. Over 1 billion gallons of biodiesel, a renewable alternative to diesel fuel, are produced each year in the US alone (US_Environmental_Protection_Agency). Composed of fatty acid methyl and ethyl esters (FAMEs and FAEEs, respectively), biodiesel is traditionally derived from the chemical transesterification of plant oils and animal fats (Hill et al., 2006). Fatty alcohols are also important oleo-chemicals and find many industrial applications ranging from lubricants to cosmetics. Traditionally, fatty alcohols are produced in two chemical steps from plant oils and animal fats: 1) transesterification/hydrolysis of plant oils and animal fats to methyl esters and fatty acids and 2) hydrogenation of methyl esters and fatty acids to fatty alcohols.

SUMMARY OF THE INVENTION

The present invention provides for a genetically modified yeast host cell capable of producing one or more fatty acids, or fatty acid-derived compounds, or a mixture thereof, comprising: (a) increased expression of acetyl-CoA carboxylase (such as ACC1), (b) increased expression of one or more fatty acid synthases (such as FAS1 and FAS2), and (c) optionally reduced expression of one or more enzymes involved in or in the β-oxidation pathway (such as peroxisomal transporters PXA1 and PXA2, and β-oxidation enzymes POX1, POX2, and POX3).

In some embodiments, the yeast host cell further comprises one or more of the following: (d) increased expression of an acyl-CoA thioesterase (such as TE), (e) increased expression of a wax-ester synthase/acyltransferase (such as WS/AT), (f) increased expression of a fatty acid acyl-CoA reductase (such as FAR), (g) increased expression of a diacylglycerol-acyltransferase (such as DGAT), and (h) increased or reduced expression of fatty-acyl-CoA synthetases (such as FAA1 and FAA4).

In some embodiments, the fatty acid-derived compound is a fatty acyl ethyl ester (FAEE), a fatty alcohol, a triacylglycerol (TAG), or a mixture thereof. In some embodiments, the fatty acid is a C12:0, C14:0, C16:0, C16:1, C18:0, or C18:1, or mixture thereof. In some embodiments, the fatty acid-derived compound is a FAEE, fatty alcohol, or TAG derived from one or more the following fatty acids: C12:0, C14:0, C16:0, C16:1, C18:0, and C18:1.

In some embodiments, when the yeast host cell is capable of producing a fatty acid, the yeast host cell further comprises: (d) increased expression of an acyl-CoA thioesterase (such as TE), and (h) optionally reduced expression of fatty-acyl-CoA synthetases (such as FAA1 and FAA4).

In some embodiments, when the yeast host cell is capable of producing a fatty acid-derived compound including a FAEE, the yeast host cell further comprises (e) increased expression of a wax-ester synthase/acyltransferase (such as WS/AT).

In some embodiments, when the yeast host cell is capable of producing a fatty acid-derived compound including a fatty alcohol, the yeast host cell further comprises (f) increased expression of a fatty acid acyl-CoA reductase (such as FAR).

In some embodiments, when the yeast host cell is capable of producing a fatty acid-derived compound including a TAG, the yeast host cell further comprises (g) increased expression of a diacylglycerol-acyltransferase (such as DGAT).

The term "increased expression" can mean a native gene having its expression increased, or the presence of a heterologous gene in the host cell, or both. Expression can be increased by having the expression increased (by the substitution of a stronger promoter or activating DNA sequences that increase expression of the promoter), or introducing one or more copies of the native, or one or more heterologous, gene each operably linked to a promoter into the host cell, such that the expression of the gene is increased constitutively or under certain growth conditions.

The term "reduced expression" can mean a native gene having its promoter and/or open reading frame (ORF) altered such that the expression of the wild-type, or active, enzyme or gene product is reduced under all or certain growth conditions. In some embodiments, the native gene is knocked out in that the host cell does not or essentially does not express the gene at all. In some embodiments, the promoter is completely or partially deleted, or the ORF is completely or partially deleted from the host cell's genome.

The present invention provides for a method of constructing a genetically modified yeast host cell of the claimed invention, comprising: (a) introducing one or two nucleic acids encoding an acetyl-CoA carboxylase (such as ACC1) operatively linked to a first promoter capable of expression in the host cell, and a fatty acid synthases (such as FAS1 and FAS2) operatively linked to a second promoter capable of expression in the host cell, and (b) optionally altering one or more promoters and/or ORFs encoding of one or more enzymes involved in or in the β-oxidation pathway (such as peroxisomal transporters PXA1 and PXA2, and β-oxidation enzymes POX1, POX2, and POX3) such that the expression of the one or more enzymes is reduced or knocked out.

In some embodiments, the method further comprises one of more of the following steps: (c) introducing a nucleic acid encoding an acyl-CoA thioesterase (such as TE) operatively linked to a promoter capable of expressing the acyl-CoA thioesterase in the host cell, (d) introducing a nucleic acid encoding a wax-ester synthase/acyltransferase (such as WS/AT) operatively linked to a promoter capable of expressing the wax-ester synthase/acyltransferase in the host cell, (e) introducing a nucleic acid encoding a fatty acid acyl-CoA reductase (such as FAR) operatively linked to a promoter capable of expressing fatty acid acyl-CoA reductase in the host cell, (f) introducing a nucleic acid encoding a diacylglycerol-acyltransferase (such as DGAT) operatively linked to a promoter capable of expressing diacylglycerol-acyltransferase reductase in the host cell, and (g) altering one or more promoters and/or ORFs encoding of one or more fatty-acyl-CoA synthetases (such as FAA1 and FAA4) such that the expression of the one or more fatty-acyl-CoA synthetases is reduced or knocked out.

In some embodiments, each introducing step can independently comprises introducing an expression cassette encoding the respective enzyme into the host cell. In some embodiments, more than one, or all, nucleic acids (each encoding an enzyme) can be the same nucleic acid.

Each of the promoter can independently be a promoter that is naturally operably linked to its respective gene, or the promoter can be heterologous to the gene to which it is linked or heterologous to the host cell.

The present invention provides for a method of producing one or more fatty acids, or fatty acid-derived compounds, or a mixture thereof, in a genetically modified yeast host cell of the claimed invention. The method comprises culturing the genetically modified yeast host cell under a suitable condition such that the culturing results in the genetically modified yeast host cell producing the one or more fatty acids, or fatty acid-derived compounds, or a mixture thereof.

In some embodiments, the method further comprises recovering the one or more fatty acids, or fatty acid-derived compounds, or a mixture thereof, and optionally chemically treating the recovered compound to produce a second compound, when combusted, can produce more energy that the combustion of the recovered compound.

In some embodiments, the method results in the production of the one or more fatty acids, or fatty acid-derived compounds, or a mixture thereof, wherein the amount of the one or more fatty acids, or fatty acid-derived compounds, or a mixture thereof, produced is more than the amount of each compound produced by the unmodified or wild-type yeast host cell in the same growth condition. In some embodiments, the amount of the one or more fatty acids, or fatty acid-derived compounds, or a mixture thereof, produced is equal to or more than any one of the amounts described herein, such as described in Example 1.

The present invention further provides for the isolated one or more fatty acids, or fatty acid-derived compounds, or a mixture thereof produced from the method of the present invention.

When an enzyme is described in the present invention, the scope of the invention includes enzymes, including non-naturally or engineered enzymes having an amino acid sequence having at least 50% identity to the amino acid sequence of a naturally occurring or known enzyme, wherein the enzyme, including non-naturally or engineered enzyme, retains all conserved amino acid residues essential for its enzymatic activity, and has an enzymatic activity that is at least all or substantially all of the naturally occurring or known enzyme.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
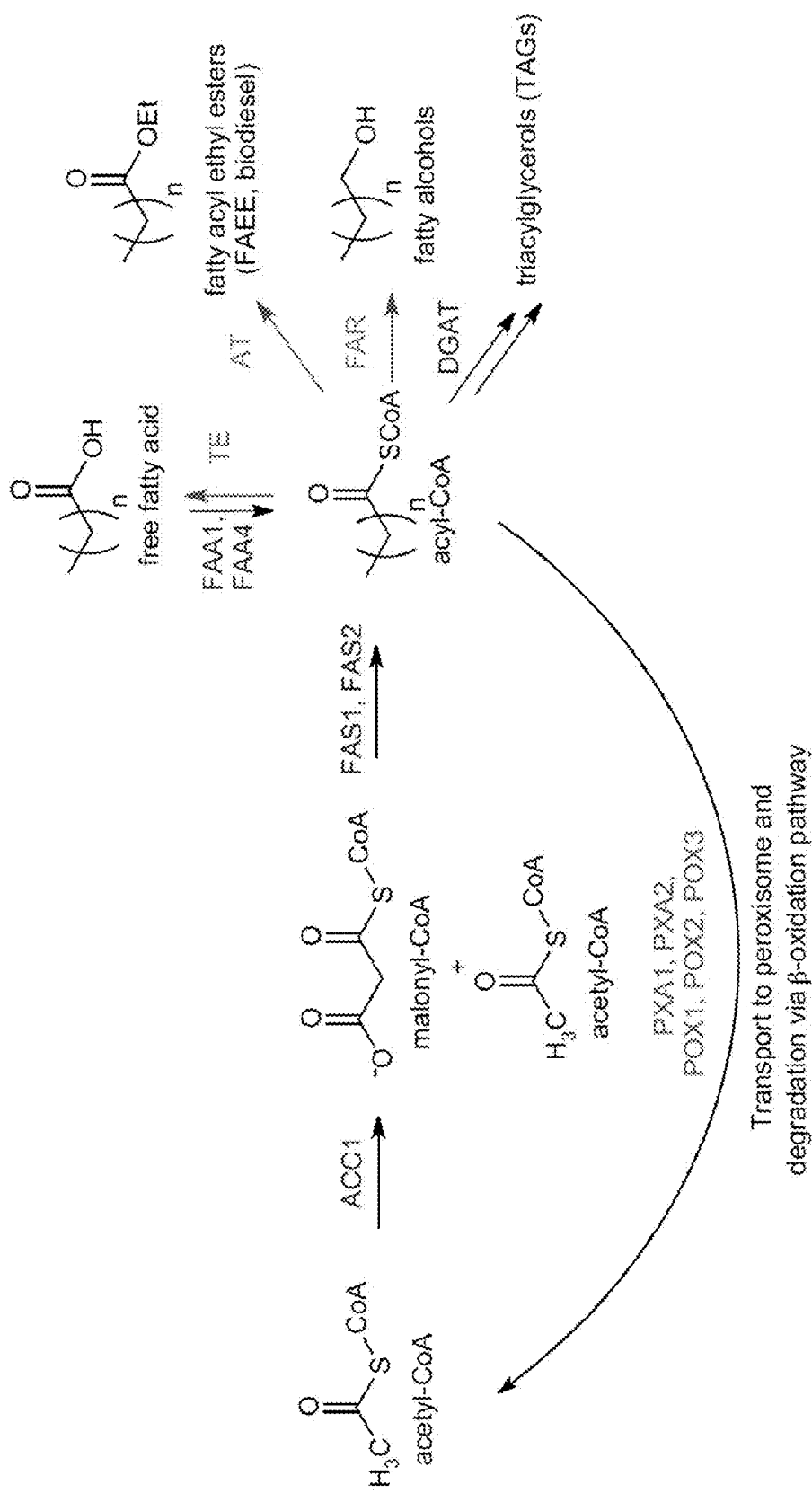
FIG. 1 shows engineered pathways for the production of fatty acid-derived molecules from simple sugars in S. cerevisiae. Flux through the native fatty acid pathway (black lines) can be increased to improve production of acyl-CoAs by overexpressing acetyl-CoA carboxylase (ACC1) and fatty acid synthases (FAS1 and FAS2), and by eliminating a portion of the β-oxidation pathway (peroxisomal transporters PXA1 and PXA2, and β-oxidation enzymes POX1, POX2 and POX3). Various products can be produced from non-native pathways (magenta lines) including free fatty acids, fatty alcohols and fatty acid ethyl esters (FAEEs or biodiesel). Free fatty acids can be produced directly from acyl-CoAs by overexpressing an acyl-CoA thioesterase (TE); fatty alcohols can be produced by overexpressing a fatty acyl-CoA reductase (FAR); and biodiesels can be produced by expressing a wax-ester synthase/acyltransferase (WS/AT).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used herein, the term "enzyme" or any of the named enzymes encompasses polymorphic variants, alleles, mutants, and interspecies homologs to the specific polypeptides described herein or known to those skilled in the art. A nucleic acid that encodes an enzyme refers to a gene, pre-mRNA, mRNA, and the like, including nucleic acids encoding polymorphic variants, alleles, mutants, and interspecies homologs of the particular amino acid sequences described herein. Thus, in some embodiments, an enzyme encodes a polypeptide having an amino acid sequence that has at least 50% amino acid sequence identity, or at least 55%, 60%, 65%, 70%, 75%, 80%, 85%, 90%, or in particular 91%, 92%, 93%, 94%, 95%, 96%, 97%, 98% or 99% or greater amino acid sequence identity, preferably over a region of at least about 25, 50, 100, 200 or more amino acids, or over the length of the entire polypeptide, to any one of the amino acid sequences shown herein.

The terms "increased expression," "increased level of activity," or "increased activity" refer interchangeably to an increase in the amount of activity of the enzyme in an engineered host cell compared to the amount of activity in a wild-type (i.e., naturally occurring) host cell. In some embodiments, increased activity results from increased expression levels. An increased level of activity or increased level of expression can be an increase in the amount of activity or expression of the enzyme in a cell genetically modified to overexpress the enzyme of at least 10%, 20%, 30%, 40%, 50%, 60%, 70%, 80%, or 90% or greater compared to a wildtype cell. Increased expression or activity of an enzyme can be assessed by any number of assays, including, but not limited to, the methods described in Example 1.

The terms "reduced expression", "reduced level of activity", "reduced activity", and "decreased activity" refer interchangeably to a reduction in the amount of activity of the enzyme in a cell engineered to decrease the enzyme compared to the amount of activity in a wild-type (i.e., naturally occurring) cell. In some embodiments, reduced activity results from reduced expression levels. A reduced level of activity or a reduced level of expression can be a reduction in the amount of activity or expression of the enzyme of at least 10%, 20%, 30%, 40%, 50%, 60%, 70%, 80%, or 90% or greater. In some embodiments, the enzyme is not reduced in amount, but is modified in amino acid sequence so that its activity is reduced directly or indirectly. Decreased expression or activity of the gene encoding the enzyme can be assessed by any number of assays, including, but not limited to, the methods described in Example 1.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a polynucleotide encoding an enzyme may have a sequence that is at least 50%, 55%, 60%, 65%, 70%, 75%, 80%, 85%, 90%, 91%, 92%, 93%, 94%, 95%, 96%, 97%, 98%, or 99% identical to a sequence of an enzyme identified herein.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another:

(1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species. A suitable promoter for the present invention is the yeast translation elongation factor-1a (TEF) promoter.

An enzyme or polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding an enzyme operably linked to a heterologous promoter.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

These and other objects, advantages, and features of the invention will become apparent to those persons skilled in the art upon reading the details of the invention as more fully described below.

In some embodiments of invention, the method further comprise the step of hydrogenating the recovered compound(s) to produce a hydrogenated fatty acid-derived compound(s), wherein the hydrogenating step is concurrent or subsequent to the recovering step; such that part or all of the recovered compound(s) is hydrogenated.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683, 195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: yeast plasmids. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. The host cell can be transformed with at least one expression vector. When only a single expression vector is used (without the addition of an intermediate), the vector will contain all of the nucleic acid sequences necessary.

The enzyme described herein can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

Any yeast host cell may be used in the present method so long as it remains viable after being transformed with a sequence of nucleic acids. Preferably, the host cell is not adversely affected by the transduction of the necessary nucleic acid sequences, the subsequent expression of the proteins (i.e., enzymes), or the resulting of any intermediates produced. Suitable yeast host cells are those of the *Saccharomyces* genus, including not limited to *S. cerevisiae*, *S. pastorianus*, and *S. carlsbergensis*.

One skilled in the art can determine the various chain lengths of the fatty acid. The chain length of the molecules can be controlled for the fatty acids.

The present invention provides for an isolated fatty acid or fatty acid-derived compound produced from the method of the present invention. Isolating the fatty acid or fatty acid-derived compound involves the separating at least part or all of the host cells, and parts thereof, from which the fatty acid or fatty acid-derived compound was produced, from the fatty acid or fatty acid-derived compound. The isolated fatty acid or fatty acid-derived compound may be free or essentially free of impurities formed from at least part or all of the host cells, and parts thereof. The isolated fatty acid or fatty acid-derived compound is essentially free of these impurities when the amount and properties of the impurities do not interfere in the use of the fatty acid or fatty acid-derived compound as a fuel, such as a fuel in a combustion reaction. These host cells are specifically cells that do not in nature produce the fatty acid or fatty acid-derived compound. The impurities are no more than 5%, 1%, 0.5%, 0.1%, 0.05%, or 0.01% by weight of a composition comprising one or more of the fatty acid or fatty acid-derived compound.

The present invention also provides for a combustible composition comprising an isolated fatty acid or fatty acid-derived compound and cellular components, wherein the cellular components do not substantially interfere in the combustion of the composition. The cellular components include whole cells or parts thereof. The cellular components are derived from host cells which produced the fatty acid or fatty acid-derived compound.

The fatty acid or fatty acid-derived compound, of the present invention are useful as fuels as chemical source of energy that can be used as an alternative to petroleum derived fuels, ethanol and the like.

In some embodiments, the host cell is a budding yeast *Saccharomyces cerevisiae* engineered to produce fatty acid-derived biofuels and chemicals from simple sugars. The host cell is capable of overexpressing all three fatty acid biosynthesis genes, namely acetyl-CoA carboxylase (ACC1), fatty acid synthase 1 (FAS1) and fatty acid synthase 2 (FAS2), in that the native promoters of all fatty acid biosynthesis genes are replaced with a strong constitutive promoter, such as TEF1 promoter (PTEF1). When coupled to triacylglycerol (TAG) production, the engineered strain is capable of accumulating lipid to more than 17% of its dry cell weight, a four-fold improvement over the control strain. In some embodiments, as TAG cannot be used directly as a fuel, the *S. cerevisiae* is optionally further engineered to produce drop-in fuels and chemicals by altering the terminal "converting enzyme"—a thioesterase, fatty acyl-CoA reductase or wax ester synthase. Such a strain is capable of producing free fatty acids at a titer of at least about 400 mg/L, fatty alcohols at least about 100 mg/L and fatty acid ethyl esters (biodiesel) at least about 5 mg/L directly from simple sugars.

Production of Triacylglyceride in *S. cerevisiae*

Overexpression of Acetyl-CoA Carboxylase (ACC)

Prior studies have highlighted the conversion of acetyl-CoA to malonyl-CoA by the enzyme acetyl-CoA carboxylase (ACC) as the rate-limiting step in fatty acid biosynthesis in many organisms including yeast. Overexpression of ACC in the oleaginous yeast *Yarrowia lypolytica* increased the lipid content 2-fold over the control, or from a lipid content of 8.8% to 17.9%. Similarly, overexpression of the four endogenous ACC genes in *E. coli* led to a six-fold increase in the rate of fatty acid biosynthesis.

In some embodiments, endogenous ACC, encoded by the ACC1 gene, is overexpressed in engineered *S. cerevisiae* to increase the pool of malonyl-CoA and subsequently the pool of fatty acyl-CoA. In some embodiments, plasmid-based overexpression of endogenous ACC1 leads to a lipid content of at least 6.8%, and at least 58% increase from a lipid content of 4.3% in the background strain BY4742. In addition, total fatty acid production can also be increased from 42.7 mg/L to at least about 63.2 mg/L.

Overexpression of Fatty Acid Synthase Complex (FAS Complex)

Overexpression of ACC1 leads to higher levels of malonyl-CoA, the primary substrate for fatty acid biosynthesis. One aspect of the present invention is the directing of this pool of malonyl-CoA into fatty acid production by overexpressing the fatty acid synthase (FAS) complex. In some embodiments, plasmid-based overexpression of both FAS1 and FAS2 leads to an at least about 30% increase in lipid content (from 4.3% to at least about 5.6%). Total fatty acid production can also be increased from 42.7 mg/L to at least about 70.6 mg/L.

Overexpression of Diacylglycerol Acyltransferase (DGAT)

The final step of triacylglycerol (TAG) biosynthesis—the acylation of diacylglycerol using acyl-CoA as the acyl donor—is catalyzed by the enzyme diacylglycerol-acyltransferase (DGAT). This step has been postulated to be a rate-limiting step in yeast lipid biosynthesis. Therefore, DGAT, which is encoded by DGA1 in *S. cerevisiae*, serves as an attractive engineering target to overproduce lipids. In previous studies, overexpression of DGAT led to increases in TAG production in plants and several strains of yeast, including *S. cerevisiae* and the oleaginous yeast *Y. lypolitica*. In one example, overexpression of DGA1 in *Y. lypolitica* led to a 4-fold increase in lipid content over the control (from 8.8% to 33.8%). Similarly, overexpression of DGA1 in a ΔSnf2 *S. cerevisiae* mutant led to a 2.7-fold increase in lipid content over the control (from 11.6% to 27%). While we were initially intrigued by this finding and had hoped to use the ΔSnf2 *S. cerevisiae* mutant as the starting strain in our metabolic engineering efforts, further investigation reveals that this mutant strain shows severe growth defects on galactose, thereby rendering it incompatible with the GAL1/GAL10 expression system, one of the most commonly used inducible expression systems in yeast. Given these considerations, we decided against using the ΔSnf2 *S. cerevisiae* mutant and opted instead to use the "wild-type" strain, *S. cerevisiae* BY4742. Plasmid-based overexpression of DGA1 led to a 150% increase in lipid content (from 4.3% to 10.9%), which corresponds to an increase in total fatty acid production from 42.7 mg/L to 168.3 mg/L.

Overexpression of Multiple Fatty Acid Biosynthesis Enzymes in *S. cerevisiae* Improved Lipid Accumulation While single-gene transformants had higher lipid contents than the empty vector controls, we speculated that simultaneously overexpressing all fatty acid biosynthesis genes would further enhance lipid production by enhancing the metabolic flux through the entire pathway. This strategy has been successfully employed in the high-titer production of amorphadiene, an isoprenoid precursor to the antimalarial drug artemisinin. The overexpression of every mevalonate pathway gene up to ERG20, coupled to the heterologous expression of amorphadiene synthase (ADS), in *S. cerevisiae* CEN.PK2 led to an amorphadiene titer of over 1.2 g/L, which is more than a five-fold increase in the production level observed in a strain where only selected genes were overexpressed.

When considering how to overexpress all of the fatty acid biosynthesis genes, we chose to chromosomally replace the native promoters of fatty acid biosynthesis genes with a strong constitutive promoter. We did not use plasmid-based overexpression of fatty acid biosynthetic genes due to the relatively large sizes of these genes (ACC1, 6702 bps; FAS1, 6156 bps; and FAS2, 5664 bps). Moreover, modifications to the host chromosome ensure genetic stability of the host strain and eliminate selection requirements. This approach has been used extensively in industry owing to the relative genetic stability of the engineered strains, which generally results in less variable production titers. To overexpress fatty acid biosynthetic enzymes in yeast, we successively replaced the native promoter of ACC1, FAS1 and FAS2 with the TEF1 promoter (PTEF1), a strong constitutive promoter. This strain, called WRY1, was used as a host strain for other "converting enzymes" to generate free fatty acids, fatty alcohols and FAEE that are non-native to yeast.

In parallel, we replaced the native promoter of DGA1 with PTEF1. This led to a 142% increase in the lipid content (from 4.3% to 10.4%), which corresponds to an increase in total fatty acid production from 42.7 mg/L to 143.3 mg/L. Since replacement of the DGA1 promoter with PTEF1 led to a lower increase in lipid content than plasmid-based overexpression of DGA1 (10.4% vs. 10.9%, respectively), we decided to overexpress DGA1 using a plasmid with a high-copy number (2 μ origin of replication). Replacement of the ACC1 promoter with PTEF1 coupled with plasmid-based overexpression of DGA1 led to a 230% increase in lipid content (from 4.3% to 14.2%), which corresponds to an increase in total fatty acid production from 42.7 mg/L to 155.0 mg/L. Similarly, replacement of both FAS1 and FAS2 promoters with PTEF1 coupled to the plasmid-based overexpression of DGA1 led to a 205% increase in lipid content (from 4.3% to 13.4%), which corresponds to an increase in total fatty acid production from 42.7 mg/L to 166.4 mg/L. Finally, replacement of ACC1, FAS1 and FAS2 promoters with PTEF1 (i.e., WRY1 strain) coupled to the plasmid-based overexpression of DGA1 led to a 302% increase in lipid content (from 4.3% to 17.3%), the highest lipid content out of all of our engineered strains. This corresponds to an increase in total fatty acid production from 42.7 mg/L to 171.5 mg/L. The distribution of fatty acids was as follows: C12:0, 3.5%; C14:0, 6.9%; C16:0, 38.3%; C16:1, 32.8%; C18:0, 6.8%; and C18:1, 11.8%. Our results demonstrate that overexpressing multiple genes gave rise to higher lipid contents than single-gene overexpression. Interestingly, while the overall lipid content was higher in these engineered strains, the biomass (dry cell weight) generated was lower than control strains. Our results suggest that overexpression of ACC1, FAS1, FAS2, and DGA1 may divert cellular resources away from biomass production towards lipid biosynthesis. This phenomenon was also observed in previous work. Specifically, Tai and colleagues observed a decrease in biomass production when ACC1 and DGA1 were both overexpressed in the oleaginous yeast *Y. lipolytica*.

Production of Free Fatty Acids in *S. cerevisiae*

Overexpression of the *E. coli* Acyl-ACP Thioesterase ('TesA) in *S. cerevisiae* LED to Production of Free Fatty Acids In *S. cerevisiae* fatty acid biosynthesis, after the last round of chain elongation, the fatty acyl-enzyme intermediate is released from the FAS synthase complex in the fatty acyl- CoA form. Fatty acids can be produced by expressing an enzyme with acyl-CoA thioesterase activity. *E. coli* TesA exhibits both acyl-ACP and acyl-CoA thioesterase activities in vivo. While expression of 'TesA (TesA lacking the membrane signal peptide at the amino-terminal end) in *E. coli* led to high levels of fatty acid production in *E. coli*, it was unclear at the outset of this study whether 'TesA would be robustly expressed and exhibit in vivo activity in *S. cerevisiae*. Gratifyingly, plasmid-based overexpression of 'TesA in *S. cerevisiae* BY4742 led to the production of 3 mg/L of free fatty acids. This is five times the production level observed in the background strain BY4742 (0.6 mg/L). We then explored whether we could improve the production of free fatty acids further by overexpressing all the fatty acid biosynthesis enzymes. Plasmid-based overexpression of 'TesA in the WRY1 strain, which has all fatty acid biosynthesis genes driven by the strong constitutive promoter PTEF1, improved production levels to 48 mg/L.

Deletion of Acyl-CoA Synthetase Genes in *S. cerevisiae* Improved Production of Free Fatty Acids Encouraged by the above results, we turned our attention to *S. cerevisiae* endogenous fatty-acyl-CoA synthetases to further improve the yield of free fatty acids. We suspect that a portion of free fatty acids produced by 'TesA are converted back to fatty acyl-CoAs by the fatty-acyl-CoA synthetases FAA1 and FAA4. Yeast has an inherent ability to break down fatty acids into acetyl-CoAs, a building block in many anabolic processes. Notably, yeast is able to survive on medium- and long-chain fatty acids as the sole carbon source. The process of breaking down fatty acids begins with the transportation of fatty acids into yeast cells. Once inside the cells, these fatty acids first need to be activated to the CoA form before they can undergo degradation through the β-oxidation pathway. To convert fatty acids into fatty acyl-CoAs, yeast expresses acyl-CoA synthetases that attach the CoA moiety to free fatty acids. *S. cerevisiae* contains five acyl-CoA synthetases (FAA1-4 and FAT1), but FAA1 and FAA4 are responsible for the majority of this activity. Therefore, fatty acyl-CoA synthetases appear to be viable engineering targets to improve production of free fatty acids. Indeed, previous engineering efforts in *E. coli* demonstrated that deletion of fadD, the *E. coli* homolog of acyl-CoA synthetase, increased the free fatty acid production by more than two-fold.

Deletion of the acyl-CoA synthetase FAA1 in *S. cerevisiae* BY4742 coupled to the plasmid-based overexpression of 'TesA led to production levels of 162 mg/L of free fatty acids. Deletion of both FAA1 and FAA4 coupled to the plasmid-based overexpression of 'TesA led to production levels of 201 mg/L of free fatty acids. To further improve fatty acid yields, we deleted both FAA1 and FAA4 in the strain WRY1, which has all fatty acid biosynthesis genes driven by the strong constitutive promoter PTEF1. Overexpression of 'TesA in the resulting strain increased free fatty yields further to 412 mg/L, a 690-fold improvement over the level observed in the reference strain (empty vector control). To the best of our knowledge, this is the highest production level of free fatty acids reported in *S. cerevisiae*. The distribution of fatty acids was as follows: C12:0, 2.7%; C14:0, 9.4%; C16:0, 47.0%; C16:1, 19.3%; C18:0, 10.4%; and C18:1, 10.7%. Remarkably, at this production level, free fatty acids that have been secreted out of the cells precipitated out of the solution. Microscopic analysis of cell cultures and GC-MS analysis of dissolved precipitates confirmed the precipitation of free fatty acids. Real-time reverse-transcription PCR (qRT-PCR) analysis of this strain confirmed high expression levels (2-3 fold higher) of ACC1, FAS1 and FAS2 over levels observed in the control strain and the absence of FAA1 and FAA4 transcripts.

Notably, our best free fatty acid-producing strain produced roughly two-fold higher total fatty acids than our best TAG-producing strain. Our results suggest that production of free fatty acids may be subjected to a less stringent level of regulation compared to the production of TAGs. Moreover, the demonstrated ability of *S. cerevisiae* to secrete some of the free fatty acids into the medium could potentially provide a driving force towards higher fatty acid production.

Production of Fatty Alcohols in *S. cerevisiae*

Overexpression of the Mouse Fatty Acyl-CoA Reductase (mFAR1) in *S. cerevisiae* Led to Production of Fatty Alcohols While free fatty acids and TAGs are valuable, choosing TAGs and free fatty acids as end fuel targets suffers from a practical standpoint. Specifically, TAGs and free fatty acids cannot be used directly as fuels and must first be converted to fatty acid alkyl esters, fatty acid-derived alkanes, alkenes or alcohols. Thus, a more direct strategy to produce fatty acid-derived biofuels via a microbial platform is to bypass TAG production altogether and convert fatty acids (in the fatty acyl-CoA form) directly to the desired fuels in vivo. To this end, we engineered *S. cerevisiae* to produce fatty alcohols and fatty acid ethyl esters (FAEEs, biodiesels) directly from simple sugars.

There is an increasingly large market for fatty alcohols, which are used in a wide range of products from surfactants (the foaming agents used in many consumer products including detergent and shampoo) to cosmetics. The global market for fatty alcohols reached $1.87 billion in 2002 and has been growing ever since. Fatty alcohols can be produced from fatty acyl-CoAs using an NAD(P)H-dependent fatty acyl-CoA reductase (FAR). Several FARs have been characterized and heterologously expressed in *E. coli* and yeast, endowing them with the ability to produce fatty alcohols. For example, our lab has previously expressed either acr1, an NADPH-dependent fatty acyl-CoA reductase from *Acinetobacter calcoaceticus* BD413, or mFAR1, an NADPH-dependent fatty acyl-CoA reductase from *Mus musculus* (mouse), in *E. coli* and showed that the engineered *E. coli* strain produced fatty alcohols up to 60 mg/L.

In this work, we overexpressed mFAR1 in *S. cerevisiae*. Gratifyingly, our engineered strains produced and exported fatty alcohols into the medium, as demonstrated by the presence of fatty alcohols in the dodecane overlay (10% v/v). The empty vector control did not produce detectable levels of fatty alcohols. Plasmid-based overexpression of mFAR1 in BY4742 led to a fatty alcohol production of 47.4 mg/L. Replacement of the native ACC1 promoter with PTef1 coupled to the plasmid-based overexpression of mFAR1 improved production levels to 56.5 mg/L. Finally, plasmid-based overexpression of mFAR1 in the WRY1 strain, which has all fatty acid biosynthesis genes driven by the strong constitutive promoter PTEF1, improved production levels to 93.4 mg/L. Deletion of POX1, the first gene in the β-oxidation pathway, did not improve fatty alcohol production titer.

Given that the reduction of one molecule of fatty acyl-CoA to fatty alcohol requires one molecule of NADPH, we explored whether increasing the pool of cytosolic NADPH would lead to an increase in fatty alcohol yield. A common strategy to achieve this is by overexpressing an NADP-dependent malic enzyme. This oxidoreductase converts malate and NADP+ to pyruvate and NADPH, releasing one molecule of carbon dioxide in the process. We overexpressed the malic enzyme from the oleaginous fungus *Mortierella alpina* in our top fatty alcohol producer strain. This led to a small increase in the final fatty alcohol titer to 98.0 mg/L. The distribution of fatty alcohols was as follows: C16:0, 91.1% and C18:0, 8.9%. To the best of our knowledge, this is the highest production level of fatty alcohols reported in *S. cerevisiae*.

Production of Fatty Acid Ethyl Esters (FAEEs) in *S. cerevisiae*

Overexpression of the Wax-Ester Synthase from *Acinetobacter calcoacericus* ADP1 (atfA) in *S. cerevisiae* LED to Production of Fatty Acid Ethyl Esters (FAEEs, Biodiesels)

We next turned our attention to fatty acid ethyl esters (biodiesels). Conversion of fatty acyl-CoAs into FAEEs requires an acyl-CoA:alcohol transferase (wax ester synthase, WS) that can accept ethanol, the most abundant short-chain alcohol in *S. cerevisiae*, as the alcohol substrate. Such an enzyme was recently identified from *Acinetobacter calcoaceticus* ADP1. The enzyme, encoded by atfA, exhibits fatty acyl-CoA: alcohol acyltransferase activity towards a broad range of alcohol substrates including ethanol. Heterologously expressing this enzyme in *E. coli*, and more recently in *S. cerevisiae* CEN.PK, led to the production of FAEEs.

In this study, overexpression of the codon-optimized atfA led to the production of FAEEs, which were detected in the dodecane layer, suggesting that the compounds were produced and secreted into the medium. Plasmid-based expression of atfA in BY4742 led to FAEE production at 1.2 mg/L. Replacement of the native ACC1 promoter with PTEF1 coupled to the plasmid-based overexpression of atfA improved production levels to 1.3 mg/L. Finally, plasmid-based overexpression of atfA in the WRY1 strain, which has all fatty acid biosynthesis genes driven by the strong constitutive promoter PTEF1, improved production levels to 4.6 mg/L. The production levels further improved slightly to 4.9 and 5.4 mg/L after the deletion of PXA2 and POX1, respectively. The latter is a 90-fold improvement over the level observed in the reference strain (empty vector control). The distribution of FAEEs was as follows: C12:0, 26.3%; C14:0, 14.9%; C16:0, 44.5%; and C18:0, 14.4%.

References Cited

Al-Feel, W., Chirala, S. S., Wakil, S. J., 1992. Cloning of the yeast FAS3 gene and primary structure of yeast acetyl-CoA carboxylase. Proc Natl Acad Sci USA. 89, 4534-8.

Beopoulos, A., Cescut, J., Haddouche, R., Uribelarrea, J. L., Molina-Jouve, C., Nicaud, J. M., 2009. *Yarrowia lipolytica* as a model for bio-oil production. Progress in lipid research. 48, 375-87.

Boeke, J. D., LaCroute, F., Fink, G. R., 1984. A positive selection for mutants lacking orotidine-5'-phosphate decarboxylase activity in yeast: 5-fluoro-orotic acid resistance. Molecular & general genetics: MGG. 197, 345-6.

Bouvier-Nave, P., Benveniste, P., Oelkers, P., Sturley, S. L., Schaller, H., 2000. Expression in yeast and tobacco of plant cDNAs encoding acyl CoA:diacylglycerol acyltransferase. European journal of biochemistry/FEBS. 267, 85-96.

Cheng, J. B., Russell, D. W., 2004. Mammalian wax biosynthesis. I. Identification of two fatty acyl-Coenzyme A reductases with different substrate specificities and tissue distributions. The Journal of biological chemistry. 279, 37789-97.

Dahlqvist, A., Stahl, U., Lenman, M., Banas, A., Lee, M., Sandager, L., Ronne, H., Stymne, S., 2000. Phospholipid: diacylglycerol acyltransferase: an enzyme that catalyzes the acyl-CoA-independent formation of triacylglycerol in yeast and plants. Proc Natl Acad Sci USA. 97, 6487-92.

Davis, M. S., Solbiati, J., Cronan, J. E., Jr., 2000. Overproduction of acetyl-CoA carboxylase activity increases the rate of fatty acid biosynthesis in *Escherichia coli*. The Journal of biological chemistry. 275, 28593-8.

Dmochowska, A., Dignard, D., Maleszka, R., Thomas, D. Y., 1990. Structure and transcriptional control of the *Saccharomyces cerevisiae* POX1 gene encoding acyl-coenzyme A oxidase. Gene. 88, 247-52.

Doan, T. T., Carlsson, A. S., Hamberg, M., Bulow, L., Stymne, S., Olsson, P., 2009. Functional expression of five *Arabidopsis* fatty acyl-CoA reductase genes in *Escherichia coli*. Journal of plant physiology. 166, 787-96.

Einerhand, A. W., Voorn-Brouwer, T. M., Erdmann, R., Kunau, W. H., Tabak, H. F., 1991. Regulation of transcription of the gene coding for peroxisomal 3-oxoacyl-CoA thiolase of *Saccharomyces cerevisiae*. European journal of biochemistry/FEBS. 200, 113-22.

Fortman, J. L., Chhabra, S., Mukhopadhyay, A., Chou, H., Lee, T. S., Steen, E., Keasling, J. D., 2008. Biofuel alternatives to ethanol: pumping the microbial well. Trends Biotechnol. 26, 375-81.

Gietz, R. D., Schiestl, R. H., 2007a. Frozen competent yeast cells that can be transformed with high efficiency using the LiAc/SS carrier DNA/PEG method. Nature protocols. 2, 1-4.

Gietz, R. D., Schiestl, R. H., 2007b. High-efficiency yeast transformation using the LiAc/SS carrier DNA/PEG method. Nature protocols. 2, 31-4.

Gueldener, U., Heinisch, J., Koehler, G. J., Voss, D., Hegemann, J. H., 2002. A second set of loxP marker cassettes for Cre-mediated multiple gene knockouts in budding yeast. Nucleic acids research. 30, e23.

Gupta, S., Dynamics of the Global Fatty Alcohol Market. 2004.

Hegemann, J. H., Heick, S. B., 2011. Delete and repeat: a comprehensive toolkit for sequential gene knockout in the budding yeast *Saccharomyces cerevisiae*. Methods Mol Biol. 765, 189-206.

Hill, J., Nelson, E., Tilman, D., Polasky, S., Tiffany, D., 2006. Environmental, economic, and energetic costs and benefits of biodiesel and ethanol biofuels. Proc. Natl Acad. Sci. USA. 103, 11206-11210.

Hiltunen, J. K., Wenzel, B., Beyer, A., Erdmann, R., Fossa, A., Kunau, W. H., 1992. Peroxisomal multifunctional beta-oxidation protein of *Saccharomyces cerevisiae*. Molecular analysis of the fox2 gene and gene product. The Journal of biological chemistry. 267, 6646-53.

Hobbs, D. H., Lu, C., Hills, M. J., 1999. Cloning of a cDNA encoding diacylglycerol acyltransferase from *Arabidopsis thaliana* and its functional expression. FEBS letters. 452, 145-9.

Jako, C., Kumar, A., Wei, Y., Zou, J., Barton, D. L., Giblin, E. M., Covello, P. S., Taylor, D. C., 2001. Seed-specific over-expression of an *Arabidopsis* cDNA encoding a diacylglycerol acyltransferase enhances seed oil content and seed weight. Plant physiology. 126, 861-74.

Johnson, B., Nelson, S. J., Brown, C. M., 1972. Influence of glucose concentration on the physiology and lipid composition of some yeasts. Antonie van Leeuwenhoek. 38, 129-36.

Kalscheuer, R., Luftmann, H., Steinbuchel, A., 2004. Synthesis of novel lipids in *Saccharomyces cerevisiae* by heterologous expression of an unspecific bacterial acyltransferase. Applied and environmental microbiology. 70, 7119-25.

Kamisaka, Y., Noda, N., Tomita, N., Kimura, K., Kodaki, T., Hosaka, K., 2006. Identification of genes affecting lipid content using transposon mutagenesis in *Saccharomyces cerevisiae*. Bioscience, biotechnology, and biochemistry. 70, 646-53.

Kamisaka, Y., Tomita, N., Kimura, K., Kainou, K., Uemura, H., 2007. DGA1 (diacylglycerol acyltransferase gene) overexpression and leucine biosynthesis significantly increase lipid accumulation in the Deltasnf2 disruptant of *Saccharomyces cerevisiae*. The Biochemical journal. 408, 61-8.

Knoll, L. J., Johnson, D. R., Gordon, J. I., 1995. Complementation of *Saccharomyces cerevisiae* strains containing fatty acid activation gene (FAA) deletions with a mammalian acyl-CoA synthetase. The Journal of biological chemistry. 270, 10861-7.

Knudsen, J., Jensen, M. V., Hansen, J. K., Faergeman, N. J., Neergaard, T. B., Gaigg, B., 1999. Role of acylCoA binding protein in acylCoA transport, metabolism and cell signaling. Molecular and cellular biochemistry. 192, 95-103.

Liu, T., Vora, H., Khosla, C., 2010. Quantitative analysis and engineering of fatty acid biosynthesis in *E. coli*. Metab Eng. 12, 378-86.

Los, M., Czyz, A., Sell, E., Wegrzyn, A., Neubauer, P., Wegrzyn, G., 2004. Bacteriophage contamination: is there a simple method to reduce its deleterious effects in laboratory cultures and biotechnological factories? Journal of applied genetics. 45, 111-20.

Lu, X., Vora, H., Khosla, C., 2008. Overproduction of free fatty acids in *E. coli*: Implications for biodiesel production. Metab. Eng. 10, 333-339.

Lynd, L. R., van Zyl, W. H., McBride, J. E., Laser, M., 2005. Consolidated bioprocessing of cellulosic biomass: an update. Curr. Opin. Biotechnol. 16, 577-583.

Magnuson, K., Jackowski, S., Rock, C. O., Cronan, J. E., Jr., 1993. Regulation of fatty acid biosynthesis in *Escherichia coli*. Microbiological reviews. 57, 522-42.

Metz, J. G., Pollard, M. R., Anderson, L., Hayes, T. R., Lassner, M. W., 2000. Purification of a jojoba embryo fatty acyl-coenzyme A reductase and expression of its cDNA in high erucic acid rapeseed. Plant physiology. 122, 635-44.

Moreira dos Santos, M., Raghevendran, V., Kotter, P., Olsson, L., Nielsen, J., 2004. Manipulation of malic enzyme in *Saccharomyces cerevisiae* for increasing NADPH production capacity aerobically in different cellular compartments. Metab Eng. 6, 352-63.

Nevoigt, E., Kohnke, J., Fischer, C. R., Alper, H., Stahl, U., Stephanopoulos, G., 2006. Engineering of promoter replacement cassettes for fine-tuning of gene expression in *Saccharomyces cerevisiae*. Applied and environmental microbiology. 72, 5266-73.

Ogiwara, H., Tanabe, T., Nikawa, J., Numa, S., 1978. Inhibition of rat-liver acetyl-coenzyme-A carboxylase by palmitoyl-coenzyme A. Formation of equimolar enzyme-inhibitor complex. European journal of biochemistry/FEBS. 89, 33-41.

Scharnewski, M., Pongdontri, P., Mora, G., Hoppert, M., Fulda, M., 2008. Mutants of *Saccharomyces cerevisiae* deficient in acyl-CoA synthetases secrete fatty acids due to interrupted fatty acid recycling. The FEBS journal. 275, 2765-78.

Schweizer, E., Hofmann, J., 2004. Microbial type I fatty acid synthases (FAS): major players in a network of cellular FAS systems. Microbiology and molecular biology reviews: MMBR. 68, 501-17.

Shani, N., Valle, D., 1996. A *Saccharomyces cerevisiae* homolog of the human adrenoleukodystrophy transporter is a heterodimer of two half ATP-binding cassette transporters. Proc Natl Acad Sci USA. 93, 11901-6.

Shi, S., Valle-Rodriguez, J. O., Khoomrung, S., Siewers, V., Nielsen, J., 2012. Functional expression and characterization of five wax ester synthases in *Saccharomyces cerevisiae* and their utility for biodiesel production. Biotechnology for biofuels. 5, 7.

Steen, E. J., 2010. Microbial production of fatty-acid-derived fuels and chemicals from plant biomass. Nature. 463, 559-562.

Steen, E. J., Kang, Y., Bokinsky, G., Hu, Z., Schirmer, A., McClure, A., del Cardayre, S. B., Keasling, J. D., 2010. Microbial production of fatty-acid-derived fuels and chemicals from plant biomass. Nature. 463, 559-562.

Stoveken, T., Kalscheuer, R., Malkus, U., Reichelt, R., Steinbuchel, A., 2005. The wax ester synthase/acyl coenzyme A:diacylglycerol acyltransferase from *Acinetobacter* sp. strain ADP1: characterization of a novel type of acyltransferase. Journal of bacteriology. 187, 1369-76.

Tai, M., Stephanopoulos, G., 2013. Engineering the push and pull of lipid biosynthesis in oleaginous yeast *Yarrowia lipolytica* for biofuel production. Metabolic engineering. 15, 1-9.

Tehlivets, O., Scheuringer, K., Kohlwein, S. D., 2007. Fatty acid synthesis and elongation in yeast. Biochimica et biophysica acta. 1771, 255-70.

Trotter, P. J., 2001. The genetics of fatty acid metabolism in *Saccharomyces cerevisiae*. Annual review of nutrition. 21, 97-119.

US_Environmental_Protection_Agency, 2012 Renewable Fuel Standards. (website for: gpo.gov/fdsys/pkg/FR-2012-01-09/pdf/2011-33451.pdf).

Vioque, J., Kolattukudy, P. E., 1997. Resolution and purification of an aldehyde-generating and an alcohol-generating fatty acyl-CoA reductase from pea leaves (*Pisum sativum* L.). Archives of biochemistry and biophysics. 340, 64-72.

Westfall, P. J., Pitera, D. J., Lenihan, J. R., Eng, D., Woolard, F. X., Regentin, R., Horning, T., Tsuruta, H., Melis, D. J., Owens, A., Fickes, S., Diola, D., Benjamin, K. R., Keasling, J. D., Leavell, M. D., McPhee, D. J., Renninger, N. S., Newman, J. D., Paddon, C. J., 2012. Production of amorphadiene in yeast, and its conversion to dihydroartemisinic acid, precursor to the antimalarial agent artemisinin. Proceedings of the National Academy of Sciences of the United States of America. 109, E111-8.

Wynn, J. P., bin Abdul Hamid, A., Ratledge, C., 1999. The role of malic enzyme in the regulation of lipid accumulation in filamentous fungi. Microbiology. 145 (Pt 8), 1911-7.

Yu, K. O., Jung, J., Kim, S. W., Park, C. H., Han, S. O., 2012. Synthesis of FAEEs from glycerol in engineered *Saccharomyces cerevisiae* using endogenously produced ethanol by heterologous expression of an unspecific bacterial acyltransferase. Biotechnology and bioengineering. 109, 110-5.

Zhang, Y., Adams, I. P., Ratledge, C., 2007. Malic enzyme: the controlling activity for lipid production? Overexpression of malic enzyme in *Mucor circinelloides* leads to a 2.5-fold increase in lipid accumulation. Microbiology. 153, 2013-25.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Metabolic Engineering of *Saccharomyces cerevisiae* for Production of Fatty Acid-Derived Biofuels and Chemicals As the serious effects of global climate change become apparent and access to fossil fuels becomes more limited, metabolic engineers and synthetic biologists are looking towards greener sources for transportation fuels. In recent years, microbial production of high-energy fuels by economically efficient bioprocesses has emerged as an attractive alternative to the traditional production of transportation fuels. Here, we engineered the budding yeast *Saccharomyces cerevisiae* to produce fatty acid-derived biofuels and chemicals from simple sugars. Specifically, we overexpressed all three fatty acid biosynthesis genes, namely acetyl-CoA carboxylase (ACC1), fatty acid synthase 1 (FAS1) and fatty acid synthase 2 (FAS2), in *S. cerevisiae*. When coupled to triacylglycerol (TAG) production, the engineered strain accumulated lipid to more than 17% of its dry cell weight, a four-fold improvement over the control strain. Understanding that TAG cannot be used directly as fuels, we also engineered *S. cerevisiae* to produce drop-in fuels and chemicals. Altering the terminal "converting enzyme" in the engineered strain led to the production of free fatty acids at a titer of approximately 400 mg/L, fatty alcohols at approximately 100 mg/L and fatty acid ethyl esters (biodiesel) at approximately 5 mg/L directly from simple sugars. We envision that our approach will provide a more scalable, controllable and economic route to this important class of chemicals.

Our lab has recently engineered *E. coli* to produce FAEEs and fatty alcohols directly from glucose at titers of up to 674 mg/L and 60 mg/L, respectively (Steen, 2010). A disadvantage of using *E. coli* as a host for FAEE and fatty alcohol production is that the direct product of fatty acid synthase enzymes is in the form of fatty acyl-ACP. This enzyme-linked product needs to be hydrolyzed by a thioesterase to free fatty acid and subsequently activated to fatty acyl-CoA by a ligase before any converting enzymes (acyltransferase to produce FAEEs or fatty acyl-CoA reductase to produce fatty alcohols) can act on them (Steen, 2010). Because the product of *S. cerevisiae* fatty acid synthase is already in the form of fatty acyl-CoA—the correct form for the "converting enzymes"—the yeast system is a more direct way to produce FAEEs and fatty alcohols. Moreover, *E. coli* is susceptible to phage attacks, which could hamper production at industrial levels (Los et al., 2004). Here, we demonstrate that engineering fatty acid biosynthesis by overexpressing key fatty acid and TAG biosynthesis enzymes augmented TAG accumulation (FIG. 1). Additionally, we developed a fatty acid-overproducer strain by replacing the native promoters of all fatty acid biosynthesis genes with a strong constitutive promoter (TEF1 promoter ($P_{TEF1}$)). Depending on the choice of terminal "converting enzyme"—a thioesterase, fatty acyl-CoA reductase or wax ester synthase—this overproducer could produce and secrete free fatty acids, fatty alcohols and FAEEs into the culture medium.

2. Materials And Methods 2.1 Yeast Strain, Media and Transformation

The yeast strains used in this study were constructed from BY4742 (derivative of S288C, (Mat α; his3Δ1; leu2Δ0; met15Δ0; ura3Δ0)) (Table 1). The yeast ΔPOX1 and ΔPXA2 knockout strains were purchased from ATCC. The other yeast knockout strains were generated using a previously reported gene disruption cassette for repeated use in *S. cerevisiae* (Gueldener et al., 2002). The plasmids used in this study are listed in Table 2.

TABLE 1

Strains used in this example.

| Strain name | Genotype | Description | Reference |
|---|---|---|---|
| BY4742 | Mat α; his3Δ1; leu2Δ0; lys2Δ0; ura3Δ0 | none | |
| BY4742 ΔPOX1 | Mat α; his3Δ1; leu2Δ0; lys2Δ0; ura3Δ0; pox1Δ | BY4742 in which POX1 has been deleted | Saccharomyces Genome Deletion Project |
| BY4742 ΔPXA2 | Mat α; his3Δ1; leu2Δ0; lys2Δ0; ura3Δ0; pxa2Δ | BY4742 in which PXA2 has been deleted | Saccharomyces Genome Deletion Project |
| BY4742 ΔFAA1 | Mat α; his3Δ1; leu2Δ0; lys2Δ0; ura3Δ0; faa1Δ | BY4742 in which FAA1 has been deleted | |
| BY4742 ΔFAA4 | Mat α; his3Δ1; leu2Δ0; lys2Δ0; ura3Δ0; faa4Δ | BY4742 in which FAA4 has been deleted | |
| BY4742 ΔFAA1 ΔFAA4 | Mat α; his3Δ1; leu2Δ0; lys2Δ0; ura3Δ0; faa1Δ; faa4Δ | BY4742 in which FAA1 and FAA4 have been deleted | |
| BY4742 $P_{TEF1}$-ACC1 | Mat α; his3Δ1; leu2Δ0; lys2Δ0; ura3Δ0; acc1::$P_{TEF1}$-ACC1 | BY4742 in which the promoter of ACC1 has been changed to TEF1 promoter | |

TABLE 1-continued

Strains used in this example.

| Strain name | Genotype | Description | Reference |
|---|---|---|---|
| BY4742 ΔPOX1 $P_{TEF1}$-ACC1 | Mat α; his3Δ1; leu2Δ0; lys2Δ0; ura3Δ0; pox1 Δ; acc1::$P_{TEF1}$-ACC1 | BY4742 in which POX1 has been deleted and the promoter of ACC1 has been changed to TEF1 promoter | |
| BY4742 ΔPXA2 $P_{TEF1}$-ACC1 | Mat α; his3Δ1; leu2Δ0; lys2Δ0; ura3Δ0; pxa2 Δ; acc1::$P_{TEF1}$-ACC1 | BY4742 in which PXA2 has been deleted and the promoter of ACC1 has been changed to TEF1 promoter | |
| BY4742 $P_{TEF1}$-FAS1-FAS2 | Mat α; his3Δ1; leu2Δ0; lys2Δ0; ura3Δ0; fas1::$P_{TEF1}$-FAS1; fas2::$P_{TEF1}$-FAS2 | BY4742 in which the promoters of FAS1 and FAS2 have been changed to TEF1 promoter | |
| BY4742 ΔPOX1 $P_{TEF1}$-FAS1-FAS2 | Mat α; his3Δ1; leu2Δ0; lys2Δ0; ura3Δ0; pox1 Δ; fas1::$P_{TEF1}$-FAS1; fas2::$P_{TEF1}$-FAS2 | BY4742 in which POX1 has been deleted and the promoters of FAS1 and FAS2 have been changed to TEF1 promoter | |
| BY4742 ΔPXA2 $P_{TEF1}$-FAS1-FAS2 | Mat α; his3Δ1; leu2Δ0; lys2Δ0; ura3Δ0; pxa2 Δ; fas1::$P_{TEF1}$-FAS1; fas2::$P_{TEF1}$-FAS2 | BY4742 in which PXA has been deleted and the promoters of FAS1 and FAS2 have been changed to TEF1 promoter | |
| WRY1 | Mat α; his3Δ1; leu2Δ0; lys2Δ0; ura3Δ0; acc1::$P_{TEF1}$-ACC1; fas1::$P_{TEF1}$-FAS1; fas2::$P_{TEF1}$-FAS2 | BY4742 in which the promoters of ACC1, FAS1 and FAS2 have been changed to TEF1 promoter | |
| BY4742 $P_{TEF1}$-DGA1 | Mat α; his3Δ1; leu2Δ0; lys2Δ0; ura3Δ0; dga1::$P_{TEF1}$-DGA1 | BY4742 in which the promoter of DGA1 has been changed to TEF1 promoter | |
| BY4742 ΔPOX1 $P_{TEF1}$-DGA1 | Mat α; his3Δ1; leu2Δ0; lys2Δ0; ura3Δ0; pox1 Δ; dga1::$P_{TEF1}$-DGA1 | BY4742 in which POX1 has been deleted and the promoter of DGA1 has been changed to TEF1 promoter | |
| BY4742 ΔPXA2 $P_{TEF1}$-DGA1 | Mat α; his3Δ1; leu2Δ0; lys2Δ0; ura3Δ0; pxa2 Δ; dga1::$P_{TEF1}$-DGA1 | BY4742 in which PXA2 has been deleted and the promoter of DGA1 has been changed to TEF1 promoter | |
| WRY1 ΔPOX1 | Mat α; his3Δ1; leu2Δ0; lys2Δ0; ura3Δ0; pox1Δ; acc1::$P_{TEF1}$-ACC1; fas1::$P_{TEF1}$-FAS1; fas2::$P_{TEF1}$-FAS2 | WRY1 in which POX1 has been deleted | |
| WRY1 ΔPXA2 | Mat α; his3Δ1; leu2Δ0; lys2Δ0; ura3Δ0; pxa2Δ; acc1::$P_{TEF1}$-ACC1; fas1::$P_{TEF1}$-FAS1; fas2::$P_{TEF1}$-FAS2 | WRY1 in which PXA2 has been deleted | |
| WRY1 ΔFAA1 | Mat α; his3Δ1; leu2Δ0; lys2Δ0; ura3Δ0; faa1Δ; acc1::$P_{TEF1}$-ACC1; fas1::$P_{TEF1}$-FAS1; fas2::$P_{TEF1}$-FAS2 | WRY1 in which FAA1 has been deleted | |

TABLE 1-continued

Strains used in this example.

| Strain name | Genotype | Description | Reference |
|---|---|---|---|
| WRY1 ΔFAA1 ΔPOX1 | Mat α; his3Δ1; leu2Δ0; lys2Δ0; ura3Δ0; faa1Δ; pox1Δ; acc1::P$_{TEF1}$-ACC1; fas1::P$_{TEF1}$-FAS1; fas2::P$_{TEF1}$-FAS2 | WRY1 in which FAA1 and POX1 have been deleted | |
| WRY1 ΔFAA1 ΔPXA2 | Mat α; his3Δ1; leu2Δ0; lys2Δ0; ura3Δ0; faa1Δ; pxa2Δ; acc1::P$_{TEF1}$-ACC1; fas1::P$_{TEF1}$-FAS1; fas2::P$_{TEF1}$-FAS2 | WRY1 in which FAA1 and PXA2 have been deleted | |
| WRY1 ΔFAA4 | Mat α; his3Δ1; leu2Δ0; lys2Δ0; ura3Δ0; faa4Δ; acc1::P$_{TEF1}$-ACC1; fas1::P$_{TEF1}$-FAS1; fas2::P$_{TEF1}$-FAS2 | WRY1 in which FAA4 has been deleted | |
| WRY1 ΔFAA4 ΔPOX1 | Mat α; his3Δ1; leu2Δ0; lys2Δ0; ura3Δ0; faa4Δ; pox1Δ; acc1::P$_{TEF1}$-ACC1; fas1::P$_{TEF1}$-FAS1; fas2::P$_{TEF1}$-FAS2 | WRY1 in which FAA4 and POX1 have been deleted | |
| WRY1 ΔFAA4 ΔPXA2 | Mat α; his3Δ1; leu2Δ0; lys2Δ0; ura3Δ0; faa4Δ; pxa2Δ; acc1::P$_{TEF1}$-ACC1; fas1::P$_{TEF1}$-FAS1; fas2::P$_{TEF1}$-FAS2 | WRY1 in which FAA4 and PXA2 have been deleted | |
| WRY1 ΔFAA1 ΔFAA4 | Mat α; his3Δ1; leu2Δ0; lys2Δ0; ura3Δ0; faa1Δ; faa4Δ; acc1::P$_{TEF1}$-ACC1; fas1::P$_{TEF1}$-FAS1; fas2::P$_{TEF1}$-FAS2 | WRY1 in which FAA1 and FAA4 have been deleted | |
| WRY1 ΔFAA1 ΔFAA4 ΔPOX1 | Mat α; his3Δ1; leu2Δ0; lys2Δ0; ura3Δ0; faa1Δ; faa4Δ; pox1Δ; acc1::P$_{TEF1}$-ACC1; fas1::P$_{TEF1}$-FAS1; fas2::P$_{TEF1}$-FAS2 | WRY1 in which FAA1, FAA4 and POX1 have been deleted | |
| WRY1 ΔFAA1 ΔFAA4 ΔPXA2 | Mat α; his3Δ1; leu2Δ0; lys2Δ0; ura3Δ0; faa1Δ; faa4Δ; pxa2Δ; acc1::P$_{TEF1}$-ACC1; fas1::P$_{TEF1}$-FAS1; fas2::P$_{TEF1}$-FAS2 | WRY1 in which FAA1, FAA4 and PXA2 have been deleted | |

TABLE 2

Plasmids used in this example.

| Plasmid name | Description |
|---|---|
| pESC-His3-FAS1-FAS2 | pESC-His3-P$_{GAL1}$-FAS1/P$_{GAL10}$-FAS2 |
| pESC-Ura3-ACC1 | pESC-Ura3-P$_{GAL10}$-ACC1 |
| pESC-Leu2d-DGA1 | pESC-Leu2d-P$_{GAL1}$-DGA1 |
| pESC-Leu2d-'TesA | pESC-Leu2d-P$_{GAL10}$-'TesA |
| pESC-Leu2d-mFAR1 | pESC-Leu2d-P$_{GAL1}$-mFAR1 |
| pESC-Leu2d-mFAR1-MaME | pESC-Leu2d-P$_{GAL1}$-mFAR1/P$_{GAL10}$-MaME |
| pESC-Leu2d-Atfa | pESC-Leu2d-P$_{GAL1}$-Atfa |
| p416Tef1-URA3 | p416-loxP-URA3-loxP-P$_{TEF1}$ |

Yeast and bacterial strains were stored in 25% glycerol at −80° C. E. coli was grown in Luria-Bertani medium. Carbenicillin at 100 μg/ml was added to the medium when required. Yeast strain BY4742 without plasmid was cultivated in YPD medium (10 g/L yeast extract, 20 g/L Bacto Peptone and 20 g/L glucose). Selection of yeast transformants with either HIS3, URA3 or LEU2 was done on a yeast minimal medium (6.7 g/L of Yeast Nitrogen Base (Difco), 20 g/L glucose, and a mixture of appropriate nucleotide bases and amino acids with dropouts (CSM-HIS, CSM-URA, CSM-LEU, CSM-HIS-URA or CSM-LEU-URA)). Yeast cells were cultivated at 30° C. in Erlenmeyer flasks closed with metal caps and shaken at 200 rpm.

Gene knockouts were generated using a previously reported gene disruption cassette for repeated use in S. cerevisiae (Gueldener et al., 2002). Gene disruption cassettes containing the URA3 selectable marker flanked by loxP sites (obtained by PCR of the pUG72 plasmid) were produced with 42 base pairs of homology on either side of each target integration site. Chromosomal replacement of native yeast promoters with P$_{TEF}$ was performed as previously described (Nevoigt et al., 2006). Oligonucleotide primers used for PCR, cloning, knock-outs, and promoter replacement in this study are included herein. Yeast cells were transformed using the Li/Ac/PEG method as previously described (Gietz and Schiestl, 2007a; Gietz and Schiestl, 2007b). Following yeast transformations, colonies were selected on minimal medium lacking uracil and confirmed via PCR. The marker gene (URA3) was removed by overexpressing the Cre recombinase to excise the selection marker between the loxP sites in the disruption cassette. This enables subsequent rounds of genomic integrations. Cre recombinase was expressed using the inducible GAL1 promoter on plasmid pSH62 (Hegemann and Heick, 2011). The strain harboring pSH62 was grown in SD medium plus 1 g/L 5-flouroorotic acid to encourage loss of the URA3 (Boeke et al., 1984). To verify the genetic stability of the engineered strains, their genomic DNA was isolated (Promega Wizard Genomic DNA Purification kit) and then subjected to a diagnostic PCR amplification that amplified regions both upstream and downstream of the integration/deletion sites. PCR products were purified (Qiagen PCR Purification kit) and then sequenced.

2.2 Plasmid Construction

Plasmid pESC-His3-FAS1-FAS2. FAS2 was amplified from *S. cerevisiae* genomic DNA using primers S1 and S2. The FAS2 amplicon was ligated to the SpeI site of pESC-His to yield pESC-His-FAS2. FAS1 was amplified from *S. cerevisiae* genomic DNA in two fragments using primers S3 and S4, and S5 and S6. The two fragments were joined together via overlap extension PCR using primers S3 and S6. The FAS1 amplicon was ligated to the BamHI/XhoI site of pESC-His-FAS2 to yield pESC-His-FAS1-FAS2.

Plasmid pESC-Ura3-ACC1. ACC1 was amplified from *S. cerevisiae* genomic DNA using primers S7 and S8. The amplicon was ligated to the NotI site of pESC-Ura.

Plasmid pESC-Leu2d-Dga1. Dga1 was amplified from *S. cerevisiae* genomic DNA using primers S9 and S10. The Kozak sequence AAACA was added 5' of the start codon to enhance expression. The amplicon was ligated to the BamHI/SalI site of pESC-Leu2d.

Plasmid pESC-Leu2d-'TesA. 'TesA was amplified from *E. coli* genomic DNA using primers S11 and S12. The Kozak sequence AAACA was added 5' of the start codon to enhance expression. The amplicon was ligated to the BglII/SpeI site of pESC-Leu2d.

Plasmid pESC-Leu2d-mFAR1. mFAR1 was amplified from pmFAR1 (Steen, 2010) using primers S13 and S14. The Kozak sequence AAACA was added 5' of the start codon to enhance expression. The amplicon was ligated to the BamHI/SalI site of pESC-Leu2d.

Plasmid pESC-Leu2d-mFAR1-MaME. The malic enzyme from *Mortierella alpina* codon-optimized for *S. cerevisiae* expression was synthesized by GenScript and was provided in the pUC57 vector. The gene was amplified from pUC57-MaME using primers S15 and S16. The Kozak sequence AAACA was added 5' of the start codon to enhance expression. The amplicon was ligated to the BglII/SpeI site of pESC-Leu2d-mFAR1 to yield pESC-Leu2d-mFAR1-MaME.

Plasmid pESC-Leu2d-atfA. The wax ester synthase (atfA), codon-optimized for *S. cerevisiae* expression, was synthesized by IDT-DNA as three gBLOCKS gene fragments. The gene was stitched together using the primer-extension PCR method with primers S17 and S18. The Kozak sequence AAACA was added 5' of the start codon to enhance expression. The amplicon was ligated to the BamHI/SalI site of pESC-Leu2d to yield pESC-Leu2d-atfA.

Plasmid p416Tef1-URA3. The plasmid for PCR amplification of the promoter replacement cassette with the URA3 selectable marker was constructed by amplifying the loxp-URA3-loxp region from pUG72 (Gueldener et al., 2002) with primers S19 and S20. The amplicon was placed 5' of the translation elongation factor-1a (TEF) promoter region in p416Tef using homologous recombination in yeast.

The following is a list of the primers useful for generating plasmid-based overexpression. The Kozak sequence is underlined.

pESC-His3-Fas1-Fas2
For Fas2
S1. Forward:
(SEQ ID NO: 1)
5' ATATATACTAGTATGAAGCCGGAAGTTGAG 3'

S2. Reverse:
(SEQ ID NO: 2)
5' ATATATACTAGTCTATTTCTTAGTAGAAACGGC 3'

For Fas1
S3. Forward1:
(SEQ ID NO: 3)
5' ATATATGGATCCAAAACAATGGACGCTTACTCCACAAGAC 3'

S4. Reverse1:
(SEQ ID NO: 4)
5' CTCCAGTTAATTTCGGAACCCGCCAAAGCCTTAA 3'

S5. Forward2:
(SEQ ID NO: 5)
5' TTAAGGCTTTGGCGGGTTCCGAAATTAACTGGAG 3'

S6. Reverse2:
(SEQ ID NO: 6)
5' ATATATCTCGAGTTAGGATTGTTCATACTTTTCCCAG 3' pESC-Ura3-Acc1
S7. Forward:
(SEQ ID NO: 7)
5' ATATATGCGGCCGCATGAGCGAAGAAAGCTTATTC 3'

S8. Reverse:
(SEQ ID NO: 8)
5' ATATATGCGGCCGCTTATTTCAAAGTCTTCAACAA 3' pESC-Leu2d-Dga1
S9. Forward:
(SEQ ID NO: 9)
5' ATATATGGATCC<u>AAAACA</u>ATGTCAGGAACATTCAATGAT 3'

S10. Forward:
(SEQ ID NO: 10)
5' ATATATGTCGACTTACCCAACTATCTTCAATTCTGC 3' pESC-Leu2d-'TesA
S11. Forward:
(SEQ ID NO: 11)
5' ATATATACTAGT<u>AAAACA</u>ATGGCGGACACGTTATTGATT 3'

S12. Reverse:
(SEQ ID NO: 12)
5' ATATATAGATCTTTATGAGTCATGATTTACTAA 3' pESC-Leu2d-mFAR1
S13. Forward:
(SEQ ID NO: 13)
5' ATATATGGATCC<u>AAAACA</u>ATGGTGAGCATCCCAGAG 3'

S14. Reverse:
(SEQ ID NO: 14)
5' ATATATGTCGACTTAGTAGCGCATGGTGGAGG 3' pESC-Leu2d-mFAR1-MaME
S15. Forward:
(SEQ ID NO: 15)
5' ATATATACTAGT<u>AAACA</u>ATGGCTTTGTCTTCATT 3'

S16. Reverse:
(SEQ ID NO: 16)
5' ATATATAGATCTTTATAAGTGTGGAGCGAAAG 3' pESC-Leu2d-Atfa-ScCodonOpt
S17. Forward:
(SEQ ID NO: 17)
5' ATATATGGATCC<u>AAAACA</u>ATGGGTAG 3'

S18. Reverse:
(SEQ ID NO: 18)
5' ATATATGTCGACTTAGTTTGCGGTT 3'

The following is a list of the primers useful for generating p416Tef1-Ura3, a plasmid usable as the template for generating promoter replacement cassettes.

Regions homologous to p416Tef1 are underlined. Regions homologous to pUG72 are italicized.

```
S19. Forward
                                        (SEQ ID NO: 19)
5' TACGCCAAGCGCGCAATTAACCCTCACTAAAGGGAACAAAAGCTG

CAGCTGAAGCTTCGTACGC 3'

S20. Reverse
                                        (SEQ ID NO: 20)
5' AAAATCTGGAAGAGTAAAAAAGGAGTAGAAACATTTTGAAGCTATG

CATAGGCCACTAGTGGATCT 3'
```

The following is a list of primers useful for replacement of native promoter with Tef1 promoter.

Regions homologous to *S. cerevisiae* chromosomes are underlined. Regions homologous to p416Tef1-Ura3 are italicized.

```
ACC1 Forward:
                                        (SEQ ID NO: 21)
5' CACAATTGTTATCGGTTCTACAATTGTTCTGCTCTCTTCAAT

CAGCTGAAGCTTCGTACG 3'

ACC1 Reverse:
                                        (SEQ ID NO: 22)
5' CATCTTCTGTGGAGAAGACTCGAATAAGCTTTCTTCGCTCAT

TAGTTCTAGAAAACTTAG 3'

FAS1 Forward:
                                        (SEQ ID NO: 23)
5' CACCGAAAAGTGTTGAACGATTCACTGCGACAATAATCAGA

GATTACAGTCAGCTGAAGCTTCGTACG 3'

FAS1 Reverse:
                                        (SEQ ID NO: 24)
5' TCTAAAGAACCGTGAGATAGGGTTAATGGTCTTGTGGAGTAA

GCGTCCATTAGTTCTAGAAAACTTAG 3'

FAS2 Forward:
                                        (SEQ ID NO: 25)
5' TTACTATATTTCCTAAATTTTCTCTGGTCTGCAGGCCAAAAC

AACAACTCAGCTGAAGCTTCGTACG 3'

FAS2 Reverse:
                                        (SEQ ID NO: 26)
5' AATTCAGTTAGCAAAATATGAGCTAATTCTTGCTCAACTTCC

GGCTTCATTAGTTCTAGAAAACTTAG 3'
```

The following is a list of primers useful for gene deletions. Regions homologous to *S. cerevisiae* chromosomes are underlined. Regions homologous to pUG72 are italicized.

```
FAA1 deletion Forward:
                                        (SEQ ID NO: 27)
5' TACAATAAAAACTAGAACAAACACAAAAGACAAAAAAA

GACAACAATATGCATAGGCCACTAGTGGATCTG 3'

FAA1 deletion Reverse:
                                        (SEQ ID NO: 28)
5' AGTGCTTTAGTATGATGAGGCTTTCCTATCATGGAAATG

TTGAT CCATTACAGCTGAAGCTTCGTACGCT 3'

FAA4 deletion Forward:
                                        (SEQ ID NO: 29)
5' TCTCTGTTCTTCACTATTTCTTGAAAAACTAAGAAGTACG

CATCAAAATGCATAGGCCACTAGTGGATCTG 3'

FAA4 deletion Reverse:
                                        (SEQ ID NO: 30)
5' TAGTGTTTATGAAGGGCAGGGGGGAAAGTAAAAAACTATG

TCTTCCTTTACAGCTGAAGCTTCGTACGCT 3'
```

The following is a list of primers useful for yeast colony PCR to verify gene deletions.

```
FAA1 upstream Forward:
5' ACCCCTCACTTGTCGTGAGAC 3'      (SEQ ID NO: 31)

URA3 Reverse:
5' TTAATGGGGAGCGCTGAT 3'         (SEQ ID NO: 32)

FAA4 upstream Forward:
5' GTTGACATAAAAGCGAGAATAC 3'     (SEQ ID NO: 33)

URA3 Reverse:
5' TTAATGGGGAGCGCTGAT 3'         (SEQ ID NO: 34)
```

The following is a list of primers useful for yeast genomic DNA PCR to verify genetic stability.

```
FAS1 upstream Forward:
5' CAGCATGTGAAAAAACCC 3'         (SEQ ID NO: 35)

FAS1 internal Reverse:
5' GGCAGTAACTACGTAGTG 3'         (SEQ ID NO: 36)

FAS2 upstream Forward:
5' CTTACTCAATTGTTTAAT 3'         (SEQ ID NO: 37)

FAS2 internal Reverse:
5' GCGAGTTTGTAAGTATTT 3'         (SEQ ID NO: 38)

ACC1 upstream Forward:
5' AAGAACAAGAACAACAAA 3'         (SEQ ID NO: 39)

ACC1 internal Reverse:
5' TGCCTTAATCATGACAGG 3'         (SEQ ID NO: 40)

TEF1 promoter Forward:
5' CCTCCCATTGATATTTAAG 3'        (SEQ ID NO: 41)

TEF1 promoter Reverse:
5' TAGTTCTAGAAAACTTAG 3'         (SEQ ID NO: 42)

FAA1 upstream Forward:
5' CCCATCGCATATCAGGAG 3'         (SEQ ID NO: 43)

FAA1 downstream Reverse:
5' GGTAATGCTTCTTATGTGAGG 3'      (SEQ ID NO: 44)

FAA4 upstream Forward:
5' TTACCCCAACAAAAACAGC 3'        (SEQ ID NO: 45)

FAA4 downstream Reverse:
5' ATAATGTCAATCTTGTCTTGC 3'      (SEQ ID NO: 46)
```

The following is a list of primers useful for qRT-PCR.

```
TAF10 Forward:
5' GCGAGAGCTAGGCAGCTATT 3'       (SEQ ID NO: 47)

TAF10 Reverse:
5' ATCGTTCACCGTCAGAACAA 3'       (SEQ ID NO: 48)
```

```
FAS1 Forward:
5' ATATTCGGTTCTGGTTTCGG 3'         (SEQ ID NO: 49)

FAS1 Reverse:
5' CCCTCGAACCAAATAGGAAA 3'         (SEQ ID NO: 50)

FAS2 Forward:
5' GCCAGAACAAGATGGGAAAT 3'         (SEQ ID NO: 51)

FAS2 Reverse:
5' TGTATGGACGACCCTTCAAA 3'         (SEQ ID NO: 52)

ACC1 Forward:
5' GGGTTACTTCTCCGTGGGTA 3'         (SEQ ID NO: 53)

ACC1 Reverse:
5' AATTCCTTCAGGGCAACAAC 3'         (SEQ ID NO: 54)

FAA1 Forward:
5' AACATGCAACGTCTCCACAT 3'         (SEQ ID NO: 55)

FAA1 Reverse:
5' TGGAGAACCACCGTTTAACA 3'         (SEQ ID NO: 56)

FAA4 Forward:
5' TGCTCATTGGATATGGGCTA 3'         (SEQ ID NO: 57)

FAA4 Reverse:
5' TAGTTCCGACAAGGTCACCA 3'         (SEQ ID NO: 58)

DGA1 Forward:
5' TTACCATCCACACGGCATAG 3'         (SEQ ID NO: 59)

DGA1 Reverse:
5' TGACCAGTGTCATCAGAGAAATAG 3'    (SEQ ID NO: 60)
```

2.3 Determination of Lipid Content in Engineered Strains

Quantification of the lipid content of engineered strains was performed as previously described with some modifications (Kamisaka et al., 2006). Strains were grown in nitrogen-limited (1 g/L ammonium sulfate) minimal medium to enhance lipid production. Strains were pre-cultured in 5-mL aliquots in minimal medium (1× yeast nitrogen base without ammonium sulfate, 1 g/L ammonium sulfate, 2% glucose, complete supplement mixture (CSM) with appropriate amino acid dropouts) overnight and used to inoculate 50 mL minimal medium (1× yeast nitrogen base without ammonium sulfate, 1 g/L, ammonium sulfate, 0.2% glucose, 1.8% galactose, and CSM with appropriate amino acid dropouts) in 250-mL flask cultures to achieve an initial $OD_{600}$ of 0.05. After 72 and 168 hours, the $OD_{600}$ was measured, and 10-mL aliquots of yeast cultures were collected and centrifuged at 3000×g for 5 min. Cell pellets were then washed once with 10 mL of distilled water and lyophilized at −45° C. for 2 days. Lyophilized cells were then weighed to obtain the dry cell weight (DCW). To transesterify total fatty acids, 1 mL of 3 N HCl in methanol (Sigma) and 0.1 mL chloroform were added to lyophilized cells. After incubation at 70° C. for 3 hours, the reaction mixture was cooled to room temperature, and 2 mL of saturated NaCl solution was added followed by 15 seconds of vortex. Two milliliters of hexane were added, and the reaction was agitated by vortex for 15 seconds. After a brief centrifugation step at 3000×g for 1 min, the hexane (top) layer containing fatty acid methyl esters (FAME) was then analyzed on gas chromatography-mass spectrometry (GC-MS) using an HP 6890 Series GC with an Agilent 5973 Network MSD equipped with a DB5 column (Thermo). The GC program was as follows: The initial temperature of 40° C. was maintained for 3 min, then ramped to 250° C. at a rate of 20° C./min and held there for 5 min. The lipid content (%) is calculated as total fatty acid amount (mg) per dry cell weight (mg)×100.

2.4 GC-MS Analysis of Free Fatty Acids, Fatty Alcohols and FAEEs

For free fatty acid production, strains were pre-cultured in 5-mL aliquots in minimal medium (1× yeast nitrogen base, 2% glucose, complete supplement mixture (CSM) with appropriate amino acid dropouts) overnight and used to inoculate 50 mL minimal medium (1× yeast nitrogen base, 0.2% glucose, 1.8% galactose, and CSM with appropriate amino acid dropouts) in 250-mL flask cultures to achieve an initial $OD_{600}$ of 0.05. After 96 hours, 100 μL of yeast culture were spiked with 1.5 μL of pentadecanoic acid standard (6 mg/mL) and then mixed with 10 μL of 40% v/v tetrabutylammonium hydroxide (TBAH) solution (Sigma). Then, 100 μL of dichloromethane (DCM)/iodomethane (MeI) was added to the sample, and the mixture was agitated by vortex for 10 seconds. The organic (bottom) layer was transferred to a GC-MS vial and the solvent was allowed to evaporate completely. Then, 100 uL of fresh DCM was added to the extract, and the samples were run using a previously described method (Steen, 2010) with some differences. The GC program was as follows: an initial temperature of 40° C. was maintained for 3 min, followed by ramping to 250° C. at a rate of 20° C./min where the temperature was held for 5 min. In cultures where white precipitates were visible, the cultures were filtered through the Nalgene Rapid-Flow filtration unit. Precipitates were collected and dissolved in 100 μL of dichloromethane (DCM)/iodomethane (MeI). Then, 1.5 μL of the pentadecanoic acid standard (6 mg/mL), 10 μL of 40% v/v tetrabutylammonium hydroxide (TBAH) solution and 100 μL of double-distilled water were added to the mixture. The mixture was agitated by vortex for 10 seconds. The organic (bottom) layer was transferred to a GC-MS vial and the solvent was allowed to evaporate completely. Then, 100 uL of fresh DCM was added to the extract, and the samples were run using the GC program as described above.

2.5 HPLC Analysis of Ethanol Accumulation in Engineered Strains

Engineered strains overproducing FAEEs were pre-cultured in 5-mL aliquots in minimal medium (1× yeast nitrogen base, 2% glucose, complete supplement mixture (CSM) with appropriate amino acid dropouts) overnight and used to inoculate 50 mL minimal medium (1× yeast nitrogen base, 0.2% glucose, 1.8% galactose, and CSM with appropriate amino acid dropouts) in 250-mL flask cultures to achieve an initial $OD_{600}$ of 0.05. After 72 and 168 hours, 1 mL of culture was centrifuged at 18,000 g for 5 min and the supernatant was applied to an Agilent 1100 series HPLC equipped with an Aminex HPX-87H ion exchange column (Biorad). The LC program was performed using 4 mM $H_2SO_4$ as the solvent at a flow rate of 0.6 mL/min. The column was maintained at 50° C. All metabolites were detected with an Agilent 1200 series DAD and RID detectors.

2.6 RNA Isolation and Transcript Quantification

Strains were pre-cultured in 5-mL aliquots in minimal medium (1× yeast nitrogen base, 2% glucose, complete supplement mixture (CSM) with appropriate amino acid dropouts) overnight and used to inoculate 50 mL of minimal medium (1× yeast nitrogen base, 0.2% glucose, 1.8% galactose, and CSM with appropriate amino acid dropouts) in 250-mL flask cultures to achieve an initial $OD_{600}$ of 0.05. After 72 h, a 5-mL aliquot of each culture was collected and centrifuged for 5 min at 3000×g. The pellets were washed with 5 mL of distilled water. Total RNA was extracted using the QIAgen RNeasy Kit under the manufacturer's protocol. Contaminating genomic DNA was removed from the RNA samples by DNaseI (NEB) digestion using the manufacturer's protocol. The RNA quantity was analyzed using a NanoDrop ND-1000 spectrophotometer (NanoDrop Technologies), and samples were stored at −80° C. until qRT-PCR analysis. Relative expression levels of FAD, FAS2, ACC1, FAA1, FAA4, and DGA1 were quantified using iScript One-step RT-PCR Kit with SYBR (Biorad) on StepOnePlus Real-time PCR Systems (Applied Biosystems). TAF10, a gene that encodes a subunit of transcription factor II D (TFIID), was used to normalize the amount of the total mRNA in all samples.

3. Results and Discussion 3.1 Overexpression of Single Fatty Acid Biosynthesis Enzyme/Enzyme Complex in *S. cerevisiae* Improved Lipid Accumulation 3.1.1 Overexpression of Acetyl-CoA Carboxylase (ACC)

Prior studies have highlighted the conversion of acetyl-CoA to malonyl-CoA by the enzyme acetyl-CoA carboxylase (ACC) as the rate-limiting step in fatty acid biosynthesis in many organisms including yeast (Tehlivets et al., 2007). Several research groups have targeted this enzyme in their metabolic engineering strategies to improve production of fatty acids and lipid content (Davis et al., 2000; Liu et al., 2010). Overexpression of ACC in the oleaginous yeast *Yarrowia lypolytica* increased the lipid content 2-fold over the control, or from a lipid content of 8.8% to 17.9% (Tai and Stephanopoulos, 2013). Similarly, overexpression of the four endogenous ACC genes in *E. coli* led to a six-fold increase in the rate of fatty acid biosynthesis (Davis et al., 2000; Liu et al., 2010). In this study, we overexpressed endogenous ACC, encoded by the ACC1 gene, in *S. cerevisiae* to increase the pool of malonyl-CoA and subsequently the pool of fatty acyl-CoA. Plasmid-based overexpression of endogenous ACC1 led to a lipid content of 6.8%, a 58% increase from a lipid content of 4.3% in the background strain BY4742 (Table 3). Notably, total fatty acid production also increased from 42.7 mg/L to 63.2 mg/L.

TABLE 3

Lipid content, yield and dry cell weight for reference and engineered S. cerevisiae strains. Lipid content is expressed as total fatty acids (mg)/dry cell weight (mg) × 100. Total fatty acid is given as means ± S.D. (n = 3) after 72 h.

| Strain | Plasmid(s) | Lipid content (%) | Total fatty acids (mg/L) | Dry cell weight (mg/L) |
|---|---|---|---|---|
| BY4742 | pESC-Leu2d | 4.3 ± 0.1 | 42.7 ± 1.0 | 0.99 ± 0.02 |
| BY4742 | pESC-His3-FAS1-FAS2 | 5.6 ± 0.6 | 70.6 ± 5.4 | 1.26 ± 0.09 |
| BY4742 | pESC-Ura3-ACC1 | 6.8 ± 0.2 | 63.2 ± 1.2 | 0.93 ± 0.02 |
| BY4742 | pESC-Leu2d-DGA1 | 10.9 ± 0.4 | 168.3 ± 4.1 | 1.54 ± 0.04 |
| BY4742 | pESC-His3-FAS1-FAS2 + pESC-Leu2d-DGA1 | 12.0 ± 1.1 | 147.1 ± 11.2 | 1.23 ± 0.07 |
| BY4742 | pESC-Ura3-ACC1 + pESC-Leu2d-DGA1 | 11.6 ± 0.2 | 153.8 ± 0.0 | 1.32 ± 0.03 |
| BY4742 $P_{TEF1}$-DGA1 | none | 10.4 ± 0.4 | 143.3 ± 5.2 | 1.38 ± 0.03 |
| BY4742 $P_{TEF1}$-FAS1-FAS2 | pESC-Leu2d-DGA1 | 13.4 ± 1.0 | 166.4 ± 9.4 | 1.24 ± 0.06 |
| BY4742 $P_{TEF1}$-ACC1 | pESC-Leu2d-DGA1 | 14.2 ± 1.7 | 155.0 ± 17.6 | 1.09 ± 0.04 |
| WRY1 | pESC-Leu2d-DGA1 | 17.3 ± 1.1 | 171.5 ± 10.0 | 0.99 ± 0.03 |
| BY4742 ΔPOX1 | pESC-Leu2d-DGA1 | 11.4 ± 0.6 | 149.9 ± 7.6 | 1.32 ± 0.02 |
| BY4742 | pESC-Leu2d- | 13.0 ± 0.8 | 141.4 ± 8.8 | 1.08 ± 0.01 |
| ΔPOX1 $P_{TEF1}$-ACC1 | DGA1 | | | |
| BY4742 ΔPXA2 | pESC-Leu2d-DGA1 | 11.6 ± 0.4 | 155.3 ± 5.5 | 1.34 ± 0.00 |
| BY4742 ΔPXA2 $P_{TEF1}$-ACC1 | pESC-Leu2d-DGA1 | 12.5 ± 1.9 | 143.5 ± 21.7 | 1.15 ± 0.04 |
| BY4742 ΔPXA2 $P_{TEF1}$-FAS1-FAS2 | pESC-Leu2d-DGA1 | 14.0 ± 1.7 | 190.3 ± 22.0 | 1.36 ± 0.06 |
| BY4742 ΔPOX1 $P_{TEF1}$-DGA1 | none | 9.8 ± 1.2 | 183.1 ± 19.5 | 1.87 ± 0.10 |
| BY4742 ΔPXA2 $P_{TEF1}$-DGA1 | none | 10.1 ± 0.8 | 170.4 ± 12.4 | 1.69 ± 0.06 |
| BY4742 ΔPOX1 $P_{TEF1}$-FAS1-FAS2 | pESC-Leu2d-DGA1 | 8.0 ± 1.2 | 79.4 ± 11.0 | 0.99 ± 0.06 |
| WRY1 ΔPOX1 | pESC-Leu2d-DGA1 | 16.6 ± 1.7 | 131.0 ± 13.5 | 0.79 ± 0.00 |
| WRY1 ΔPXA2 | pESC-Leu2d-DGA1 | 16.2 ± 1.7 | 140.0 ± 14.0 | 0.86 ± 0.03 |

This improvement of total lipid is considerably lower than those observed under similar strategies in *E. coli* (Liu et al., 2010). Indeed, our results are consistent with other works done in eukaryotic organisms, where overexpression of ACC generally leads to a small improvement of lipid production. Cumulatively, these results underscore the strict level of metabolic and regulatory control over this enzyme.

3.1.2 Overexpression of Fatty Acid Synthase Complex (FAS Complex)

Based on our results and previous work, we speculate that overexpression of ACC1 led to higher levels of malonyl-CoA, the primary substrate for fatty acid biosynthesis. We directed this pool of malonyl-CoA into fatty acid production by overexpressing the fatty acid synthase (FAS) complex. Plasmid-based overexpression of both FAS1 and FAS2 led to a 30% increase in lipid content (from 4.3% to 5.6%) (Table 3). Total fatty acid production also increased from 42.7 mg/L to 70.6 mg/L.

3.1.3 Overexpression of Diacylglycerol Acyltransferase (DGAT)

The final step of triacylglycerol (TAG) biosynthesis—the acylation of diacylglycerol using acyl-CoA as the acyl donor—is catalyzed by the enzyme diacylglycerol-acyltransferase (DGAT). This step has been postulated to be a rate-limiting step in yeast lipid biosynthesis (Bouvier-Nave et al., 2000; Dahlqvist et al., 2000). Therefore, DGAT, which is encoded by DGA1 in *S. cerevisiae*, serves as an attractive engineering target to overproduce lipids. In previous studies, overexpression of DGAT led to increases in TAG production in plants and several strains of yeast, including *S. cerevisiae* and the oleaginous yeast *Y. lypolitica* (Bouvier-Nave et al., 2000; Hobbs et al., 1999; Jako et al., 2001; Kamisaka et al., 2007; Tai and Stephanopoulos, 2013). In one example, overexpression of DGA1 in *Y. lypolitica* led to a 4-fold increase in lipid content over the control (from 8.8% to 33.8%) (Tai and Stephanopoulos, 2013). Similarly, overexpression of DGA1 in a ΔSnf2 *S. cerevisiae* mutant led to a 2.7-fold increase in lipid content over the control (from 11.6% to 27%) (Kamisaka et al., 2007). While we were initially intrigued by this finding and had hoped to use the ΔSnf2 *S. cerevisiae* mutant as the starting strain in our metabolic engineering efforts, further investigation reveals that this mutant strain shows severe growth defects on galactose, thereby rendering it incompatible with the GAL1/GAL10 expression system, one of the most commonly used inducible expression systems in yeast. Given these considerations, we decided against using the ΔSnf2 *S. cerevisiae* mutant and opted instead to use the "wild-type" strain, *S. cerevisiae* BY4742. Plasmid-based overexpression of DGA1 led to a 150% increase in lipid content (from 4.3% to 10.9%), which corresponds to an increase in total fatty acid production from 42.7 mg/L to 168.3 mg/L (Table 3). Real-time reverse-transcription PCR (qRT-PCR) analysis of this strain confirmed high expression level of DGA1 over the level observed in the control strain.

3.2 Overexpression of Multiple Fatty Acid Biosynthesis Enzymes in *S. cerevisiae* Improved Lipid Accumulation While single-gene transformants had higher lipid contents than the empty vector controls, we speculated that simultaneously overexpressing all fatty acid biosynthesis genes would further enhance lipid production by enhancing the metabolic flux through the entire pathway. This strategy has been successfully employed in the high-titer production of amorphadiene, an isoprenoid precursor to the antimalarial drug artemisinin (Westfall et al., 2012). The overexpression of every mevalonate pathway gene up to ERG20, coupled to the heterologous expression of amorphadiene synthase (ADS), in *S. cerevisiae* CEN.PK2 led to an amorphadiene titer of over 1.2 g/L, which is more than a five-fold increase in the production level observed in a strain where only selected genes were overexpressed.

When considering how to overexpress all of the fatty acid biosynthesis genes, we chose to chromosomally replace the native promoters of fatty acid biosynthesis genes with a strong constitutive promoter (Nevoigt et al., 2006). We did not use plasmid-based overexpression of fatty acid biosynthetic genes due to the relatively large sizes of these genes (ACC1, 6702 bps; FAS1, 6156 bps; and FAS2, 5664 bps). Moreover, modifications to the host chromosome ensure genetic stability of the host strain and eliminate selection requirements. This approach has been used extensively in industry owing to the relative genetic stability of the engineered strains, which generally results in less variable production titers. To overexpress fatty acid biosynthetic enzymes in yeast, we successively replaced the native promoter of ACC1, FAS1 and FAS2 with the TEF1 promoter ($P_{TEF1}$), a strong constitutive promoter. This strain, called WRY1, was used as a host strain for other "converting enzymes" to generate free fatty acids, fatty alcohols and FAEE that are non-native to yeast.

In parallel, we replaced the native promoter of DGA1 with $P_{TEF1}$. This led to a 142% increase in the lipid content (from 4.3% to 10.4%), which corresponds to an increase in total fatty acid production from 42.7 mg/L to 143.3 mg/L (Table 3). Since replacement of the DGA1 promoter with $P_{TEF1}$ led to a lower increase in lipid content than plasmid-based overexpression of DGA1 (10.4% vs. 10.9%, respectively), we decided to overexpress DGA1 using a plasmid with a high-copy number (2 μ origin of replication). Replacement of the ACC1 promoter with $P_{TEF1}$ coupled with plasmid-based overexpression of DGA1 led to a 230% increase in lipid content (from 4.3% to 14.2%), which corresponds to an increase in total fatty acid production from 42.7 mg/L to 155.0 mg/L. Similarly, replacement of both FAS1 and FAS2 promoters with $P_{TEF1}$ coupled to the plasmid-based overexpression of DGA1 led to a 205% increase in lipid content (from 4.3% to 13.4%), which corresponds to an increase in total fatty acid production from 42.7 mg/L to 166.4 mg/L. Finally, replacement of ACC1, FAS1 and FAS2 promoters with $P_{TEF1}$ (i.e., WRY1 strain) coupled to the plasmid-based overexpression of DGA1 led to a 302% increase in lipid content (from 4.3% to 17.3%), the highest lipid content out of all of our engineered strains. This corresponds to an increase in total fatty acid production from 42.7 mg/L to 171.5 mg/L. The distribution of fatty acids was as follows: C12:0, 3.5%; C14:0, 6.9%; C16:0, 38.3%; C16:1, 32.8%; C18:0, 6.8%; and C18:1, 11.8%. Diagnostic PCR amplification of the genomic DNA confirmed the genetic stability of the engineered strains (Supplementary FIG. S6). Real-time reverse-transcription PCR (qRT-PCR) analysis of the engineered strains confirmed high expression levels (7-16 fold for native promoter replacement with $P_{TEF1}$ and 22-250 fold for plasmid-based overexpression) of ACC1, FAS1, FAS2 and DGA1 over levels observed in the control strain (FIG. 9). Our results demonstrate that overexpressing multiple genes gave rise to higher lipid contents than single-gene overexpression. Interestingly, while the overall lipid content was higher in these engineered strains, the biomass (dry cell weight) generated was lower than control strains (Table 3). Our results suggest that overexpression of ACC1, FAS1, FAS2, and DGA1 may divert cellular resources away from biomass production towards lipid biosynthesis. This phenomenon was also observed in previous work (Tai and Stephanopoulos, 2013). Specifically, Tai and colleagues observed a decrease in biomass production when ACC1 and DGA1 were both overexpressed in the oleaginous yeast *Y. lipolytica*.

3.3 Deletion of Genes in the β-Oxidation Pathway Did not Improve Lipid Accumulation Further.

To further increase TAG production we aimed to down-regulate the β-oxidation pathway, which breaks down fatty acyl-CoAs to acetyl-CoA, a key carbon building block for many metabolic pathways. In *S. cerevisiae*, β-oxidation of fatty acids occurs solely in the peroxisome. The import of fatty acids in the acyl-CoA form into the peroxisomes requires the transporters PXA1 and PXA2 (Shani and Valle, 1996). Once inside the peroxisomes, acyl-CoA is oxidized to trans-2-enoyl-CoA by acyl-CoA oxidase, which is encoded by the POX1 gene (Dmochowska et al., 1990). Trans-2-enoyl-CoA is subsequently hydrated and oxidized to 3-ketoacyl-CoA by a bifunctional protein encoded by the POX2 gene (Hiltunen et al., 1992). The final cleavage of the ketoacyl to yield acetyl-CoA and the shortened acyl-CoA is catalyzed by a thiolase, which is encoded by the FOX3 gene (Einerhand et al., 1991). Our lab and others have successfully exploited the analogous β-oxidation pathway to improve fatty acid productions in *E. coli* (Liu et al., 2010; Lu et al., 2008; Steen et al., 2010). Deletion of FadE, the *E. coli* homolog of POX1, led to three- to four-fold increase in the fatty acid titer.

We chose to delete PXA2, which encodes a key component of the peroxisomal transporter, and POX1, which encodes the first enzyme in the oxidation pathway. Replacement of the ACC1, FAS1 and FAS2 promoters with $P_{TEF1}$ (i.e., WRY1 strain) coupled to the deletion of PXA2 and the plasmid-based overexpression of DGA1 led to a 277% increase in lipid content (from 4.3% to 16.2%) (Table 3). This corresponds to an increase in total fatty acid production from 42.7 mg/L to 140.0 mg/L. Similarly, replacement of ACC1, FAS1 and FAS2 promoters with $P_{TEF1}$ coupled to the deletion of POX1 and the plasmid-based overexpression of DGA1 led to a 286% increase in lipid content (from 4.3% to 16.6%). This corresponds to an increase in total fatty acid production from 42.7 mg/L to 131.0 mg/L. Notably, the lipid content and biomass (dry cell weight) are higher in the original strains, where the β-oxidation pathway genes are present. This suggests that, unlike in *E. coli*, the β-oxidation pathway may not be an ideal engineering target for further improving lipid production in *S. cerevisiae*.

3.4 Production of Free Fatty Acids in *S. cerevisiae*

Our mixed success in improving lipid accumulation in *S. cerevisiae* underscores the intricate and strict regulation of fatty acid and TAG biosynthesis in *S. cerevisiae*. Indeed, the extent to which *S. cerevisiae* and other yeast species ensure proper lipid homeostasis is well documented (Tehlivets et al., 2007). For example, both ACC and the FAS complex are regulated at the transcriptional, translational and post-translational levels. Furthermore, fatty acyl-CoA, an intermediate linking fatty acid production and TAG biosynthesis, is itself an inhibitor of ACC (Ogiwara et al., 1978). This level of regulation may hamper our ability to engineer a lipid overproducer that surpasses oleaginous yeast strains (a lipid content of over 20%). Therefore, we contend that, by choosing an alternative target that is non-native to yeast or one that is subjected to a lower level of regulation, we may be able to improve the production yield more freely. To this end, we turn our attention to free fatty acids. While there have been significant efforts to increase TAG production in *S. cerevisiae* and other yeasts, fewer efforts have been focused on engineering *S. cerevisiae* overproducers of free fatty acids.

Figure 2:
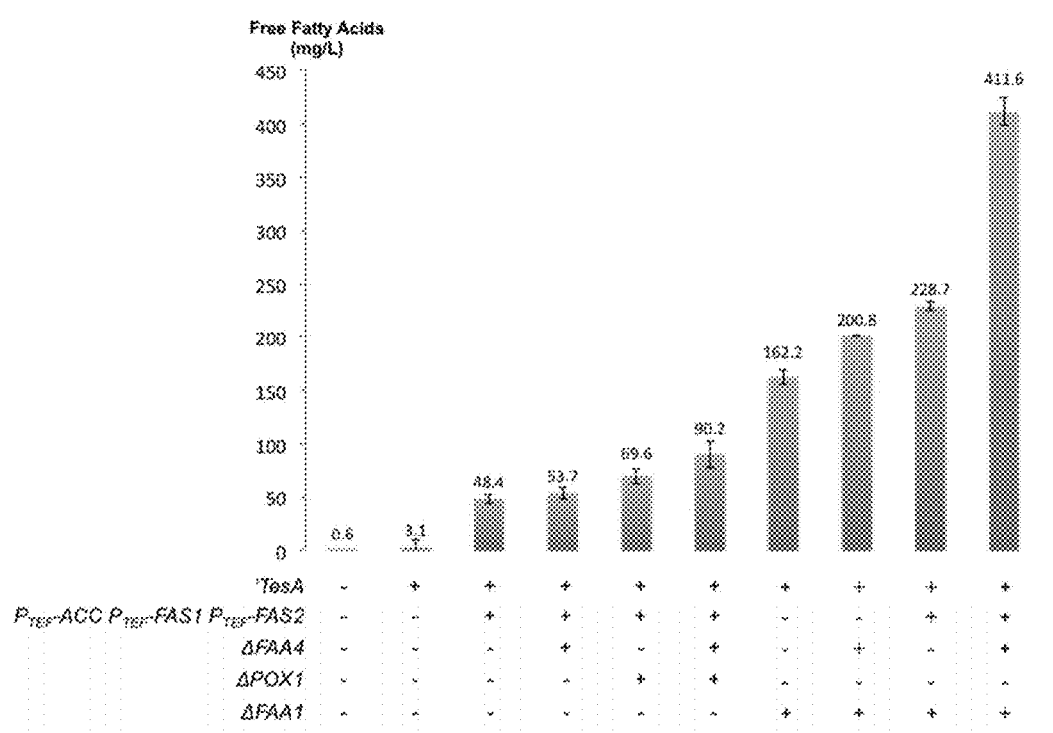
FIG. 2 shows free fatty acid production in the E. coli acyl-ACP thioesterase-expressing and control strains. All strains were cultured in minimal medium lacking the appropriate amino acid and/or nucleotide and containing a mixed carbon source (0.2% glucose and 1.8% galactose). Values are the mean of three biological replicates±standard deviation (n=3) after 96 h.

3.4.1 Overexpression of the *E. coli* Acyl-ACP Thioesterase ('TesA) in *S. cerevisiae* LED to Production of Free Fatty Acids In *S. cerevisiae* fatty acid biosynthesis, after the last round of chain elongation, the fatty acyl-enzyme intermediate is released from the FAS synthase complex in the fatty acyl-CoA form (Tehlivets et al., 2007). Fatty acids can be produced by expressing an enzyme with acyl-CoA thioesterase activity. *E. coli* TesA exhibits both acyl-ACP and acyl-CoA thioesterase activities in vivo (Steen, 2010). While expression of TesA (TesA lacking the membrane signal peptide at the amino-terminal end) in *E. coli* led to high levels of fatty acid production in *E. coli*, it was unclear at the outset of this study whether 'TesA would be robustly expressed and exhibit in vivo activity in *S. cerevisiae*. Gratifyingly, plasmid-based overexpression of TesA in *S. cerevisiae* BY4742 led to the production of 3 mg/L of free fatty acids (FIG. 2). This is eight times the production level observed in the background strain BY4742 (0.6 mg/L). We then explored whether we could improve the production of free fatty acids further by overexpressing all the fatty acid biosynthesis enzymes. Plasmid-based overexpression of 'TesA in the WRY1 strain, which has all fatty acid biosynthesis genes driven by the strong constitutive promoter $P_{TEF1}$, improved production levels to 52 mg/L.

3.4.2 Deletion of Acyl-CoA Synthetase Genes in *S. cerevisiae* Improved Production of Free Fatty Acids Encouraged by the above results, we turned our attention to *S. cerevisiae* endogenous fatty-acyl-CoA synthetases to further improve the yield of free fatty acids. We suspect that a portion of free fatty acids produced by 'TesA are converted back to fatty acyl-CoAs by the fatty-acyl-CoA synthetases FAA1 and FAA4. Yeast has an inherent ability to break down fatty acids into acetyl-CoAs, a building block in many anabolic processes (Trotter, 2001). Notably, yeast is able to survive on medium- and long-chain fatty acids as the sole carbon source. The process of breaking down fatty acids begins with the transportation of fatty acids into yeast cells. Once inside the cells, these fatty acids first need to be activated to the CoA form before they can undergo degradation through the β-oxidation pathway. To convert fatty acids into fatty acyl-CoAs, yeast expresses acyl-CoA synthetases that attach the CoA moiety to free fatty acids. *S. cerevisiae* contains five acyl-CoA synthetases (FAA1-4 and FAT1), but FAA1 and FAA4 are responsible for the majority of this activity (Trotter, 2001). The deletion of both FAA1 and FAA4 in *S. cerevisiae* renders the organism unable to survive on fatty acids as the sole carbon source, though notably the single-gene deletion of either gene does not (Knoll et al., 1995). Interestingly, when grown on other carbon sources such as glucose and raffinose, the FAA1 and FAA4 double deletion mutant is able to secrete free fatty acids into the culture medium (Scharnewski et al., 2008). Therefore, fatty acyl-CoA synthetases appear to be viable engineering targets to improve production of free fatty acids. Indeed, previous engineering efforts in *E. coli* demonstrated that deletion of fadD, the *E. coli* homolog of acyl-CoA synthetase, increased the free fatty acid production by more than two-fold (Steen, 2010).

Figure 5A:
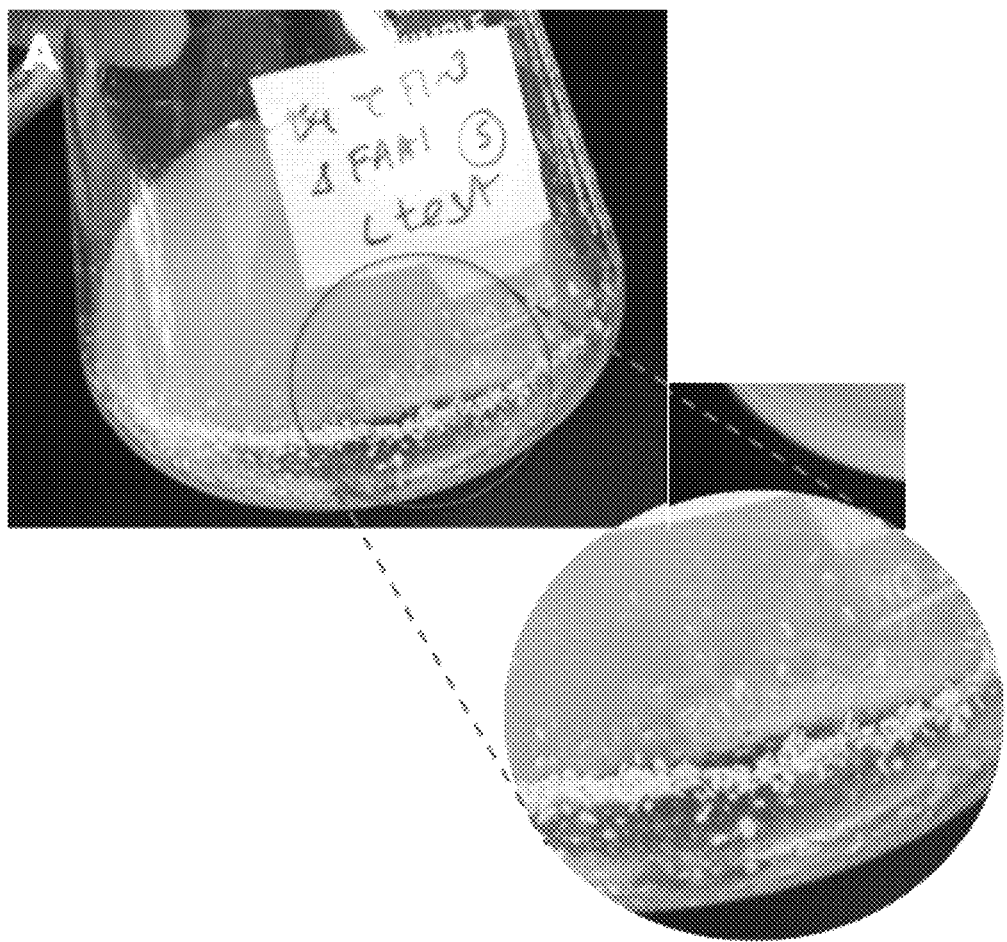
FIG. 5A shows the precipitation of fatty acid salts out of the culture medium in free fatty acid overproducer (WYR1 ΔFAA1+'TesA overexpression) after 96 h.
Figure 5B:
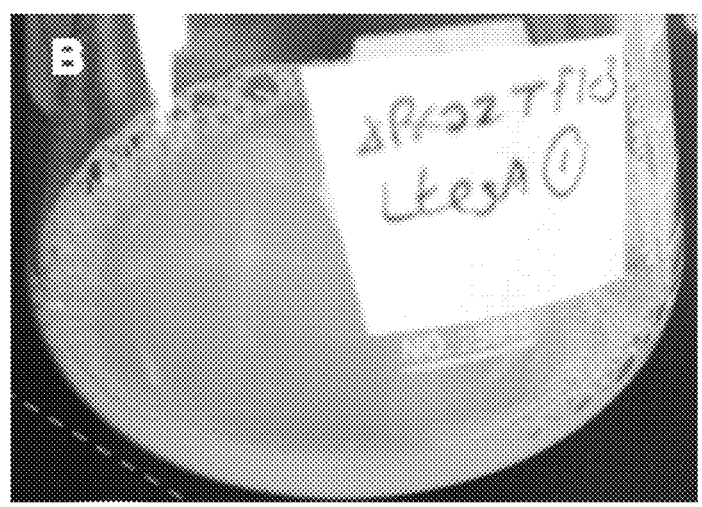
FIG. 5B shows the absence of fatty acid precipitation from a selected fatty acid producer (WYR1 ΔPXA2+'TesA overexpression) with fatty acid production levels less than 200 mg/L.
Figure 6:
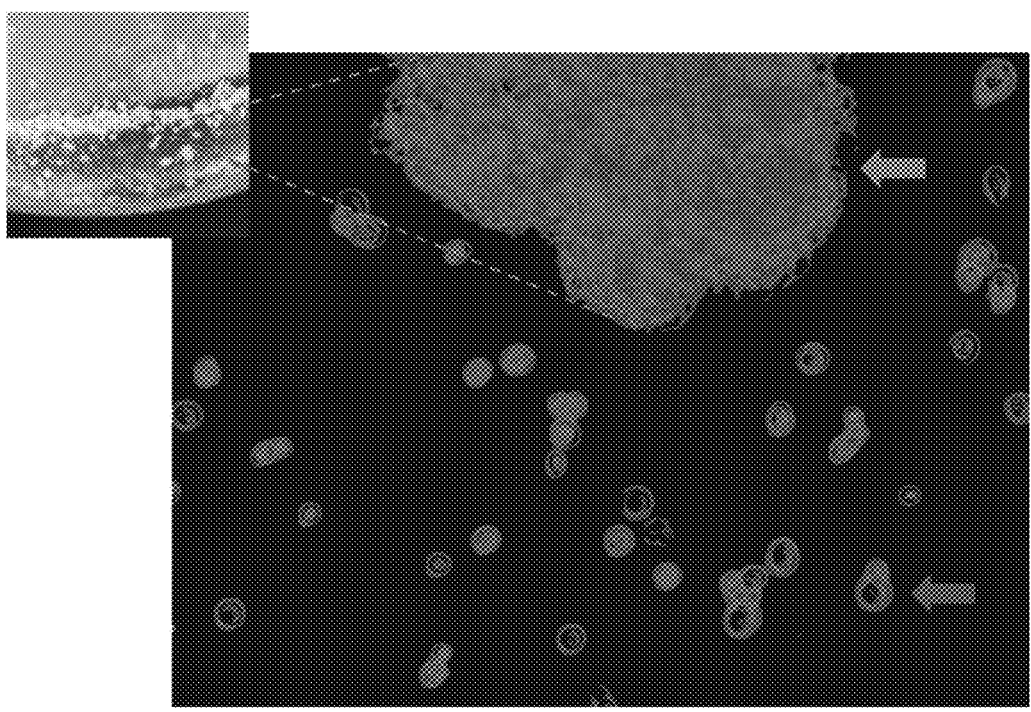
FIG. 6 shows microscopic analysis of free fatty acid overproducer (WYR1 ΔFAA1+'TesA overexpression) cell culture after 96 h. Top arrow=precipitation of fatty acid salts out of the culture medium. Bottom arrow=yeast cells.
Figure 7:
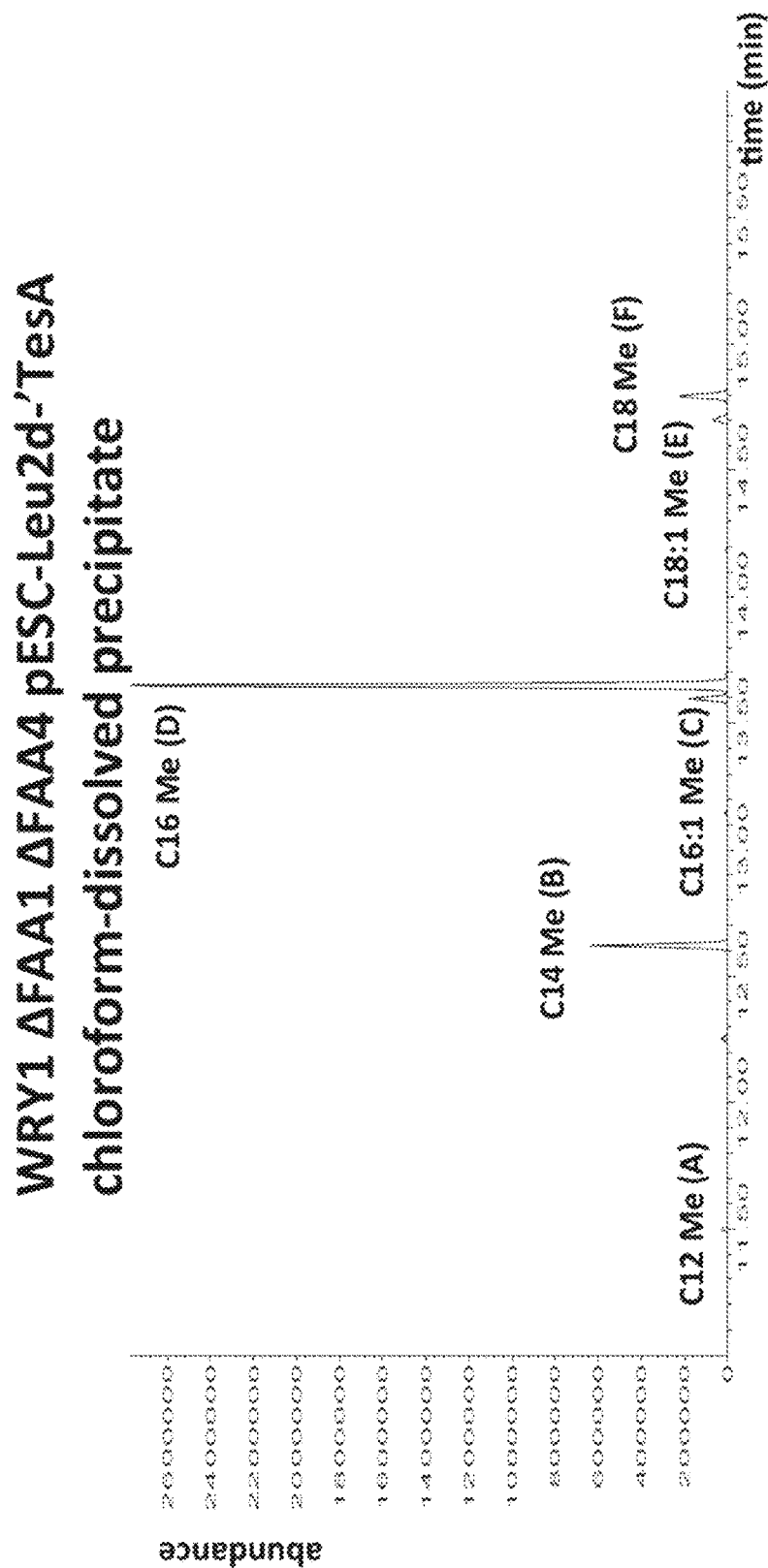
FIG. 7A shows extracted GC-MS traces of dissolved precipitates that were collected from free fatty acid over-producer (WRY1 ΔFAA1 ΔFAA4+'TesA overexpression) cell culture after 96 h (m/z 74).
FIG. 7B shows mass spectra of C12 Me.
FIG. 7C shows mass spectra of C14 Me.
FIG. 7D shows mass spectra of C16:1 Me.
FIG. 7E shows mass spectra of C16 Me.
FIG. 7F shows mass spectra of C18:1 Me.
FIG. 7G shows mass spectra of C18 Me.
Figure 7B:
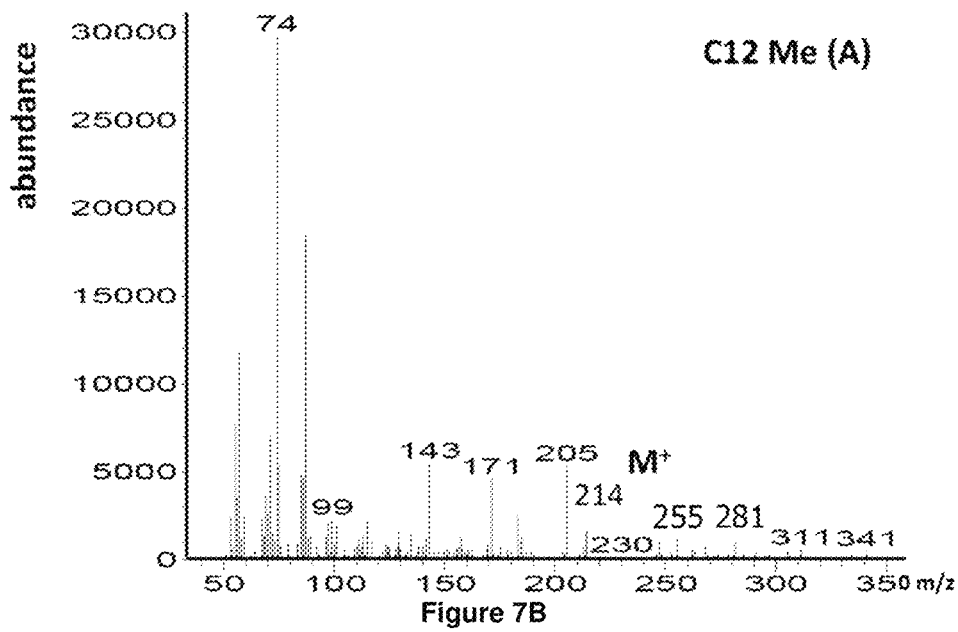
Figure 7C:
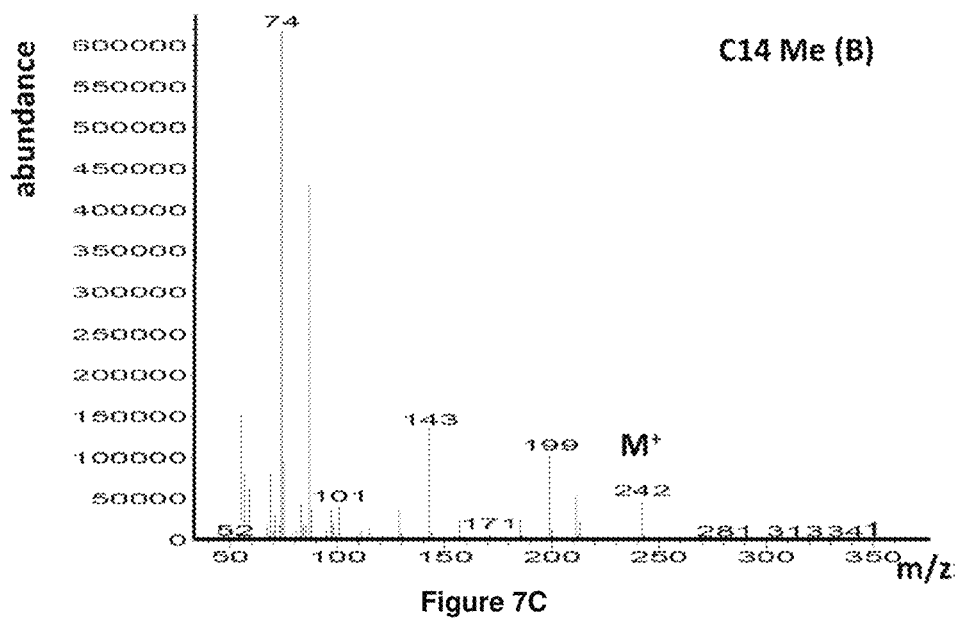
Figure 7D:
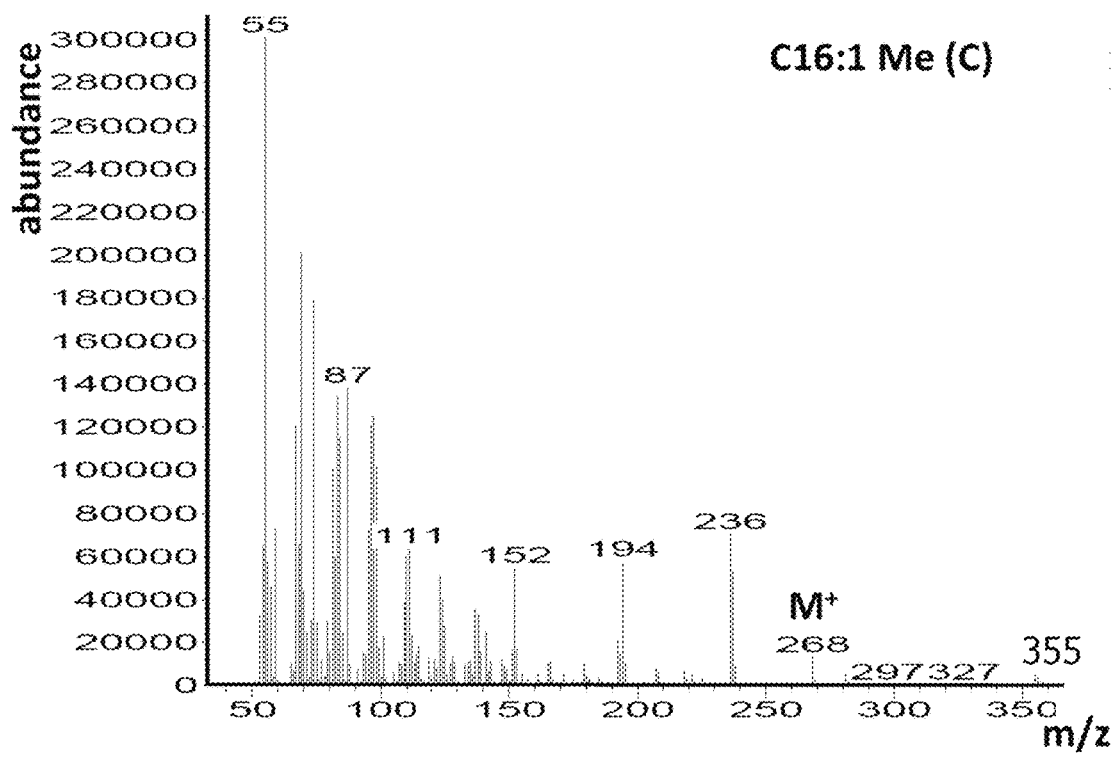
Figure 7E:
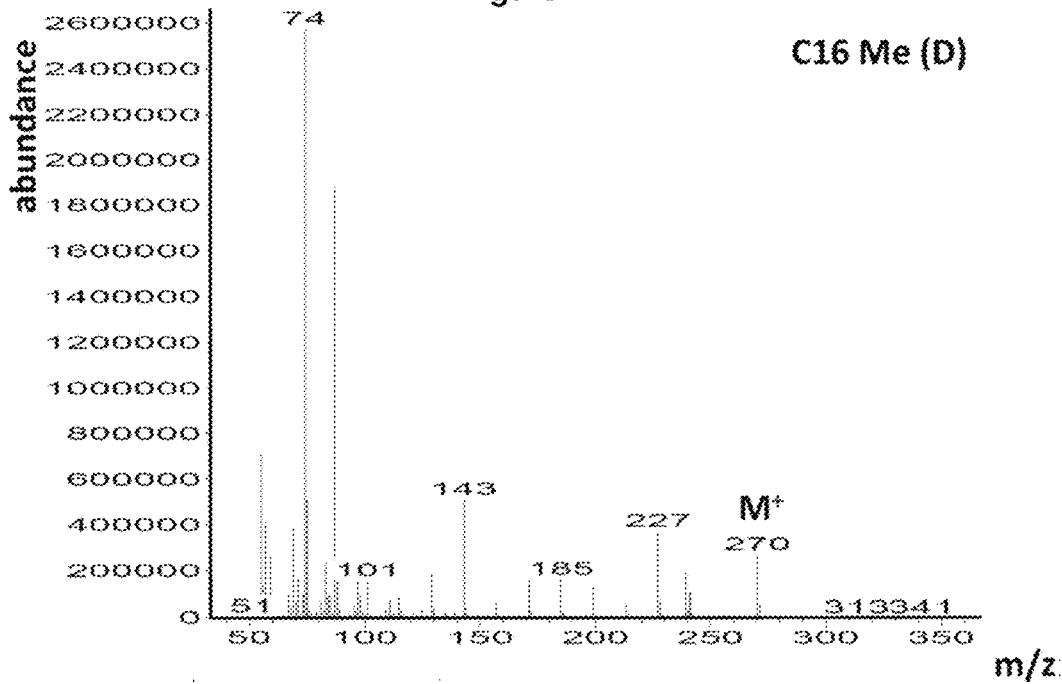
Figure 7F:
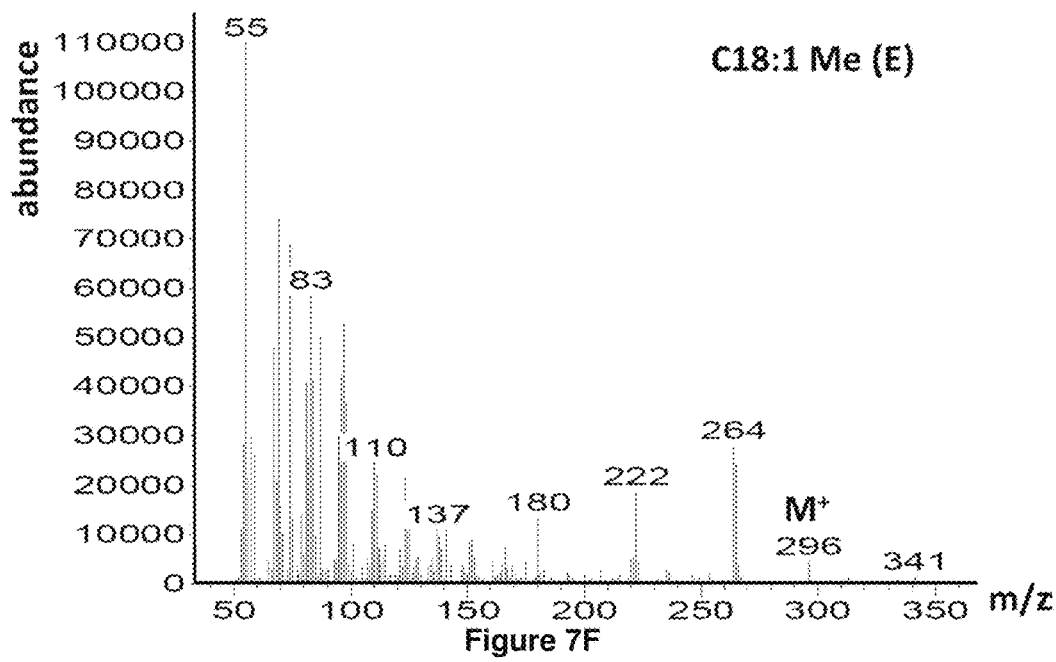
Figure 7G:
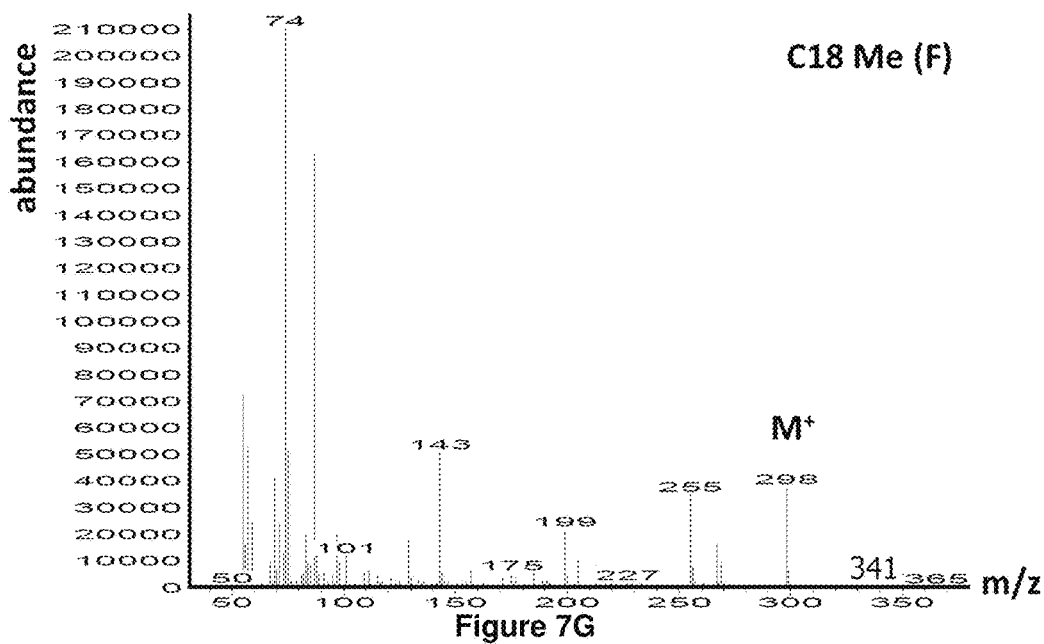
Figure 8:
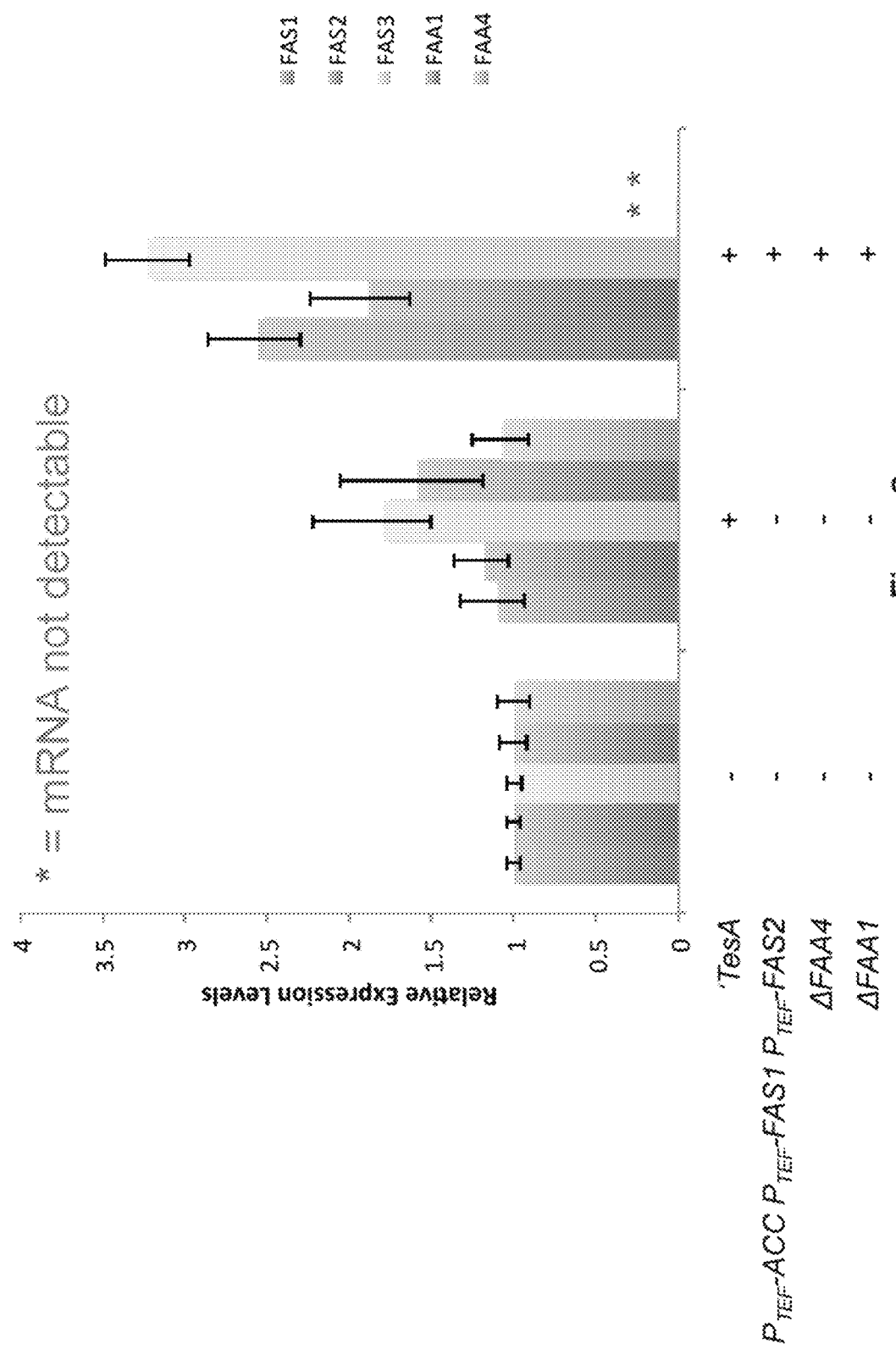
FIG. 8 shows real-time reverse-transcription PCR (qRT-PCR) analysis of engineered free fatty acid-overproducers. TAF10, a gene that encodes a subunit of transcription factor II D (TFIID), was used to normalize the amount of the total mRNA in all samples.
Figure 9A:
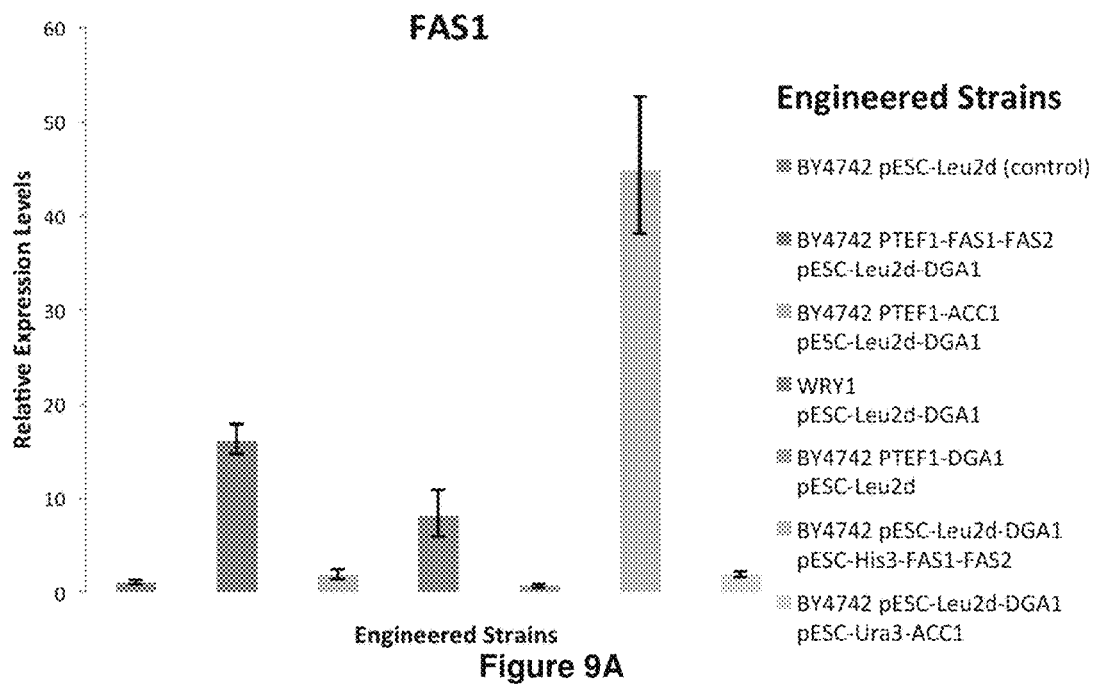
FIG. 9A shows real-time reverse-transcription PCR (qRT-PCR) analysis of engineered triacylglyceride-overproducers. TAF10, a gene that encodes a subunit of transcription factor II D (TFIID), was used to normalize the amount of the total mRNA in all samples.
Figure 9B:
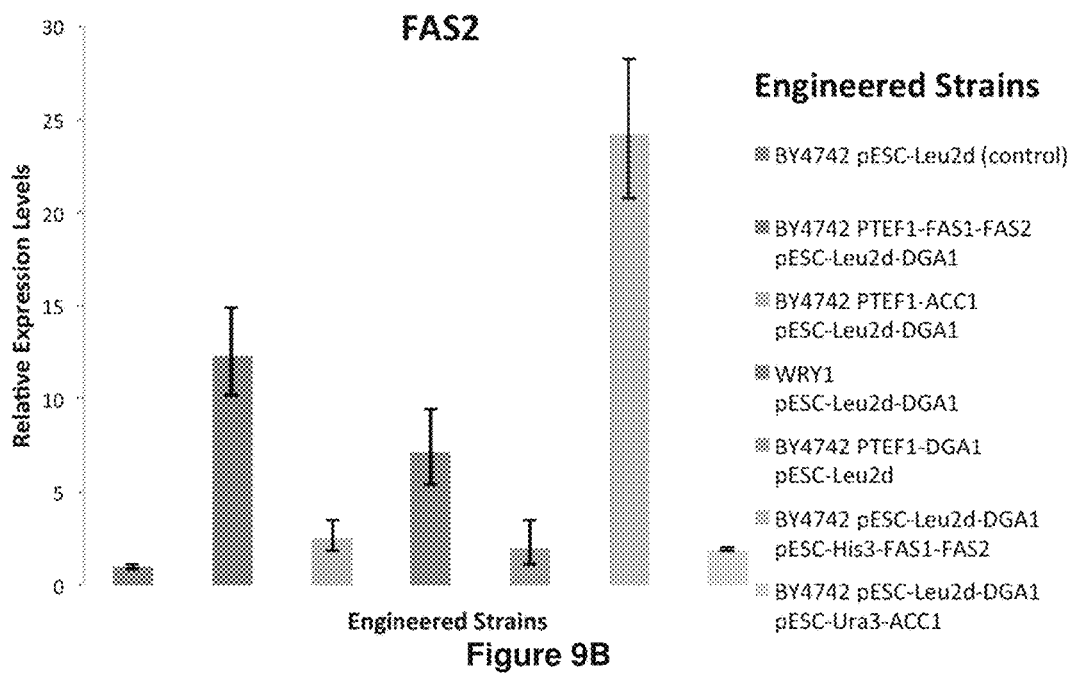
FIG. 9B shows real-time reverse-transcription PCR (qRT-PCR) analysis of engineered triacylglyceride-overproducers. TAF10, a gene that encodes a subunit of transcription factor II D (TFIID), was used to normalize the amount of the total mRNA in all samples.
Figure 9C:
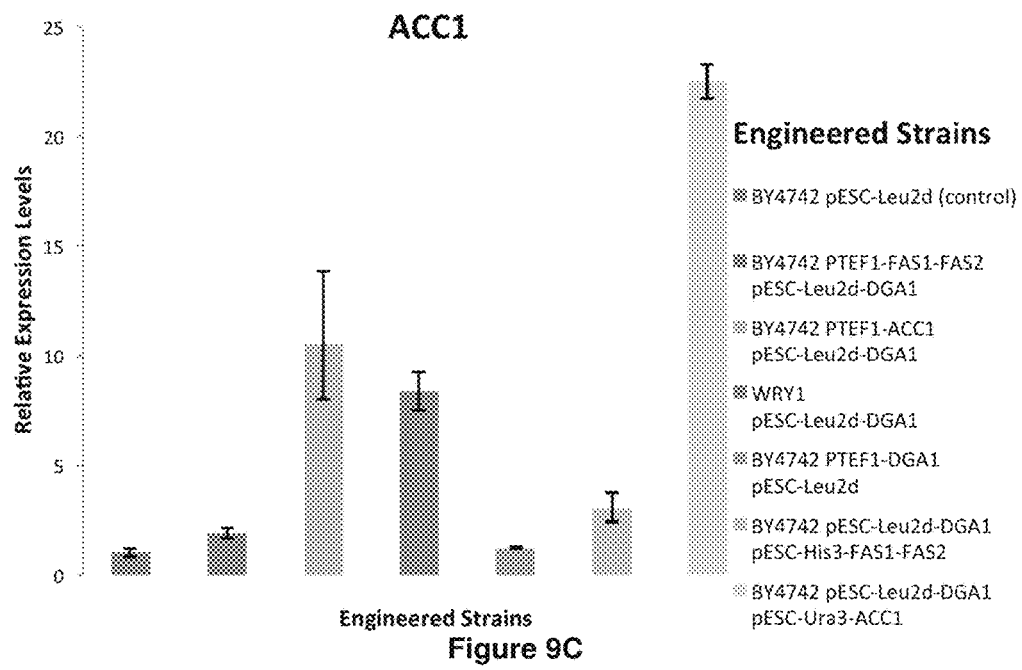
FIG. 9C shows real-time reverse-transcription PCR (qRT-PCR) analysis of engineered triacylglyceride-overproducers. TAF10, a gene that encodes a subunit of transcription factor II D (TFIID), was used to normalize the amount of the total mRNA in all samples.
Figure 9D:
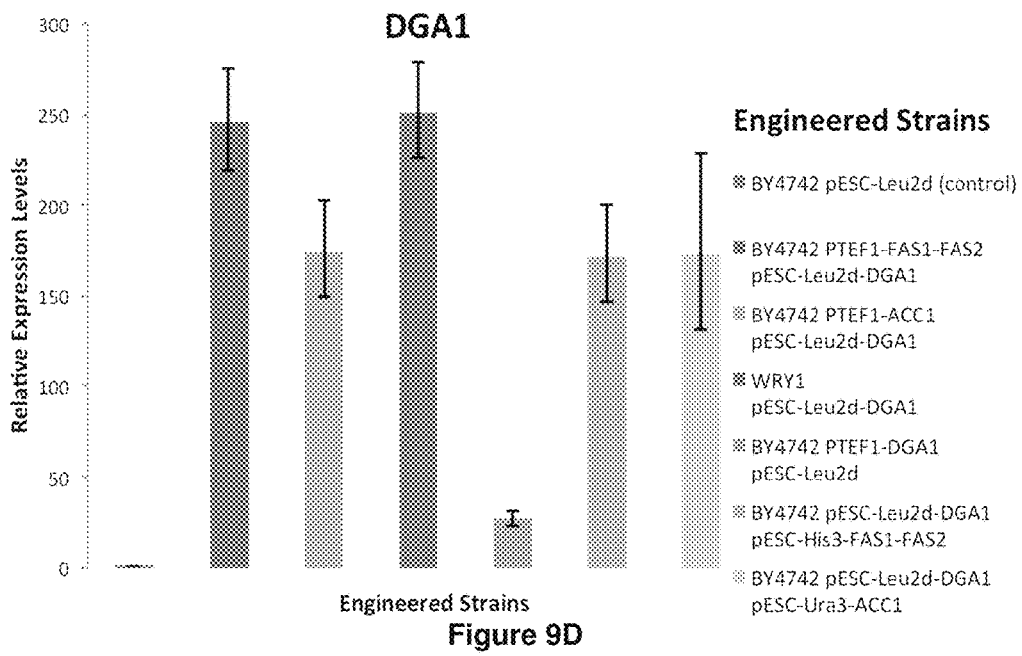
FIG. 9D shows real-time reverse-transcription PCR (qRT-PCR) analysis of engineered triacylglyceride-overproducers. TAF10, a gene that encodes a subunit of transcription factor II D (TFIID), was used to normalize the amount of the total mRNA in all samples.
Figure 10:
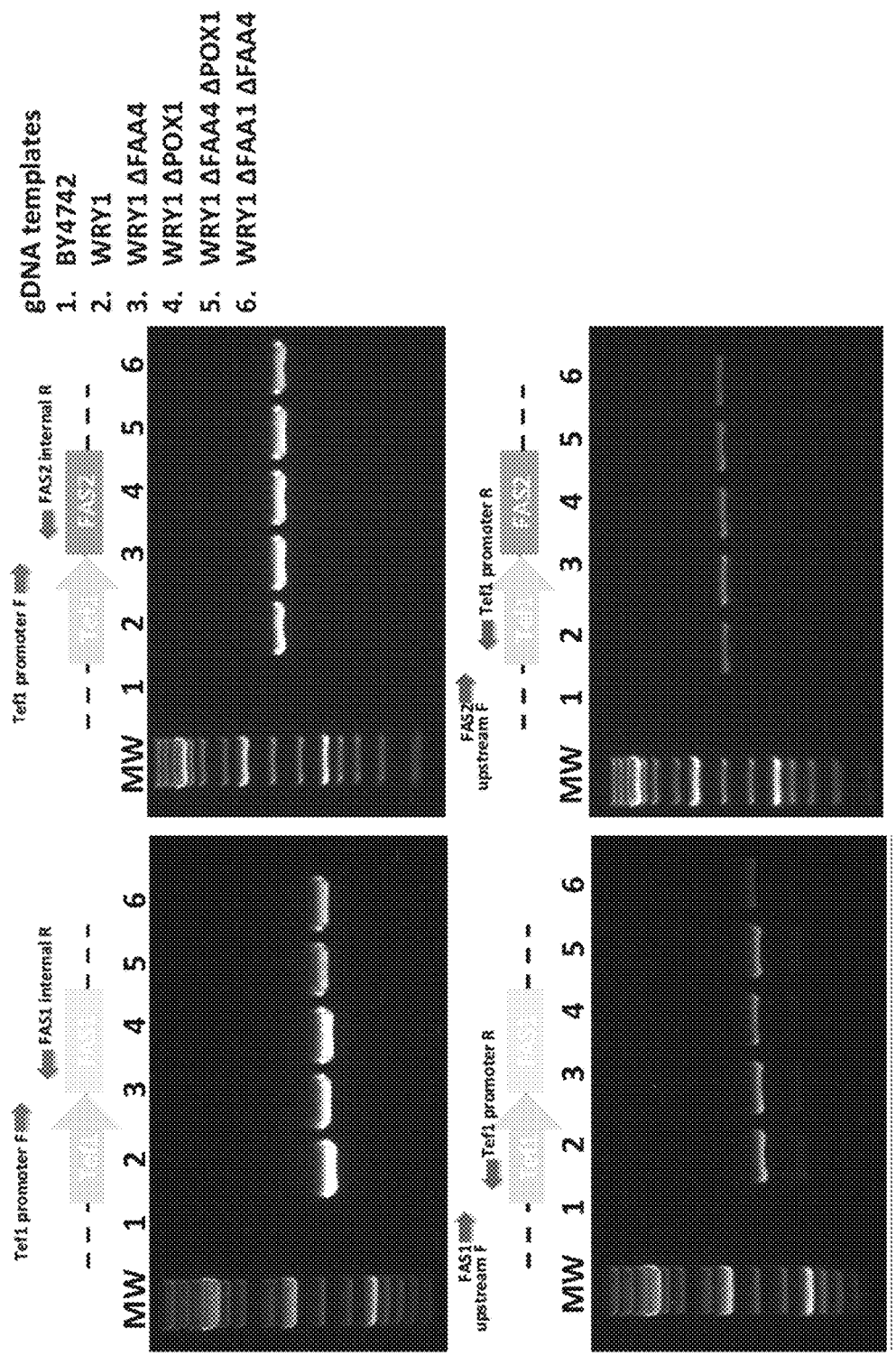
FIG. 10A shows 1% agarose gel of PCR amplification of genomic DNA from engineered and control strains. The genomic DNA templates for each gel are: Lane 1, BY4742 (control); Lane 2, WRY1; Lane 3, WRY1 ΔFAA4; Lane 4, WRY1 ΔPOX1; Lane 5, WRY1 ΔFAA4 ΔPOX1; Lane 6, WRY1 ΔFAA1 ΔFAA4. Oligonucleotide primers used for each diagnostic PCRs are illustrated over the gel. The nucleotide sequences are described in Example 1 herein.
FIG. 10B shows 1% agarose gel of PCR amplification of genomic DNA from engineered and control strains. The genomic DNA templates for each gel are: Lane 1, BY4742 (control); Lane 2, WRY1; Lane 3, WRY1 ΔFAA4; Lane 4, WRY1 ΔPOX1; Lane 5, WRY1 ΔFAA4 ΔPOX1; Lane 6, WRY1 ΔFAA1 ΔFAA4. Oligonucleotide primers used for each diagnostic PCRs are illustrated over the gel. The nucleotide sequences are described in Example 1 herein.
Figure 10:
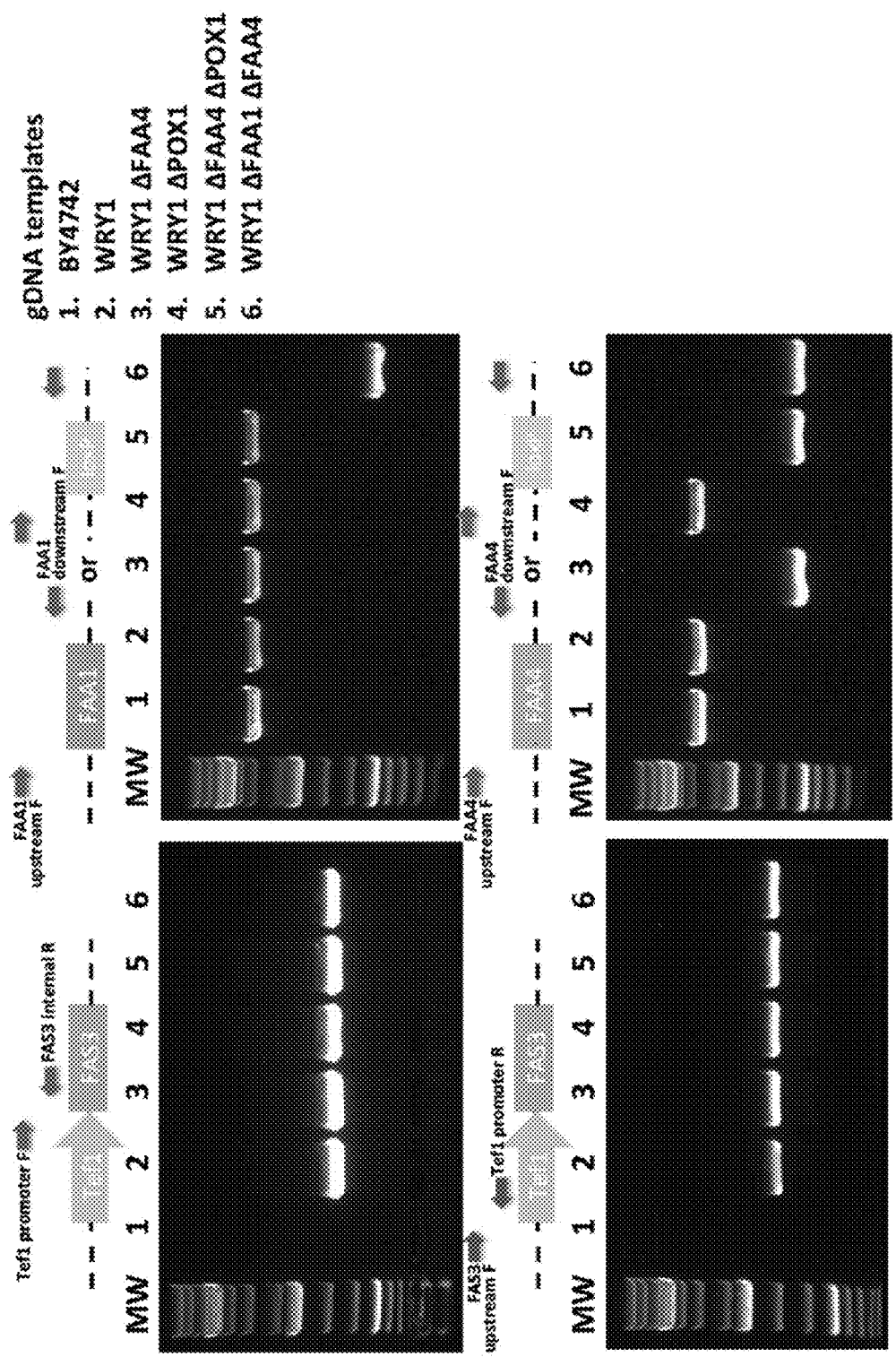

Deletion of the acyl-CoA synthetase FAA1 in *S. cerevisiae* BY4742 coupled to the plasmid-based overexpression of 'TesA led to production levels of 164 mg/L of free fatty acids (FIG. 2). Deletion of both FAA1 and FAA4 coupled to the plasmid-based overexpression of 'TesA led to production levels of 207 mg/L of free fatty acids. To further improve fatty acid yields, we deleted both FAA1 and FAA4 in the strain WRY1, which has all fatty acid biosynthesis genes driven by the strong constitutive promoter $P_{TEF1}$. Overexpression of 'TesA in the resulting strain increased free fatty yields further to 400 mg/L, a 670-fold improvement over the level observed in the reference strain (empty vector control). To the best of our knowledge, this is the highest production level of free fatty acids reported in *S. cerevisiae*. The distribution of fatty acids was as follows: C12:0, 2.7%; C14:0, 9.4%; C16:0, 47.0%; C16:1, 19.3%; C18:0, 10.4%; and C18:1, 10.7%. Remarkably, at this production level, free fatty acids that have been secreted out of the cells precipitated out of the solution (see FIG. 5). Microscopic analysis of cell cultures and GC-MS analysis of dissolved precipitates confirmed the precipitation of free fatty acids (FIGS. 6 and 7). Real-time reverse-transcription PCR (qRT-PCR) analysis of this strain confirmed high expression levels (2-3 fold higher) of ACC1, FAS1 and FAS2 over levels observed in the control strain and the absence of FAA1 and FAA4 transcripts (FIG. 8).

Notably, our best free fatty acid-producing strain produced roughly two-fold higher total fatty acids than our best TAG-producing strain (Table 3 and FIG. 2). Our results suggest that production of free fatty acids may be subjected to a less stringent level of regulation compared to the production of TAGs. Moreover, the demonstrated ability of *S. cerevisiae* to secrete some of the free fatty acids into the medium could potentially provide a driving force towards higher fatty acid production.

3.5 Production of Fatty Alcohols and Fatty Acid Ethyl Esters (FAEEs) in *S. cerevisiae*

While free fatty acids and TAGs are valuable, choosing TAGs and free fatty acids as end fuel targets suffers from a practical standpoint. Specifically, TAGs and free fatty acids cannot be used directly as fuels and must first be converted to fatty acid alkyl esters, fatty acid-derived alkanes, alkenes or alcohols. Thus, a more direct strategy to produce fatty acid-derived biofuels via a microbial platform is to bypass TAG production altogether and convert fatty acids (in the fatty acyl-CoA form) directly to the desired fuels in vivo. To this end, we engineered *S. cerevisiae* to produce fatty alcohols and fatty acid ethyl esters (FAEEs, biodiesels) directly from simple sugars.

3.5.1 Overexpression of the Mouse Fatty Acyl-CoA Reductase (mFAR1) in *S. cerevisiae* LED to Production of Fatty Alcohols There is an increasingly large market for fatty alcohols, which are used in a wide range of products from surfactants (the foaming agents used in many consumer products including detergent and shampoo) to cosmetics. The global market for fatty alcohols reached $1.87 billion in 2002 and has been growing ever since (Gupta, 2004). Fatty alcohols can be produced from fatty acyl-CoAs using an NAD(P)H-dependent fatty acyl-CoA reductase (FAR). Several FARs have been characterized and heterologously expressed in *E. coli* and yeast, endowing them with the ability to produce fatty alcohols (Cheng and Russell, 2004; Doan et al., 2009; Metz et al., 2000; Steen, 2010; Vioque and Kolattukudy, 1997). For example, our lab has previously expressed either acr1, an NADPH-dependent fatty acyl-CoA reductase from *Acinetobacter calcoaceticus* BD413, or mFAR1, an NADPH-dependent fatty acyl-CoA reductase from *Mus musculus* (mouse), in *E. coli* and showed that the engineered *E. coli* strain produced fatty alcohols up to 60 mg/L (Steen, 2010).

Figure 3:
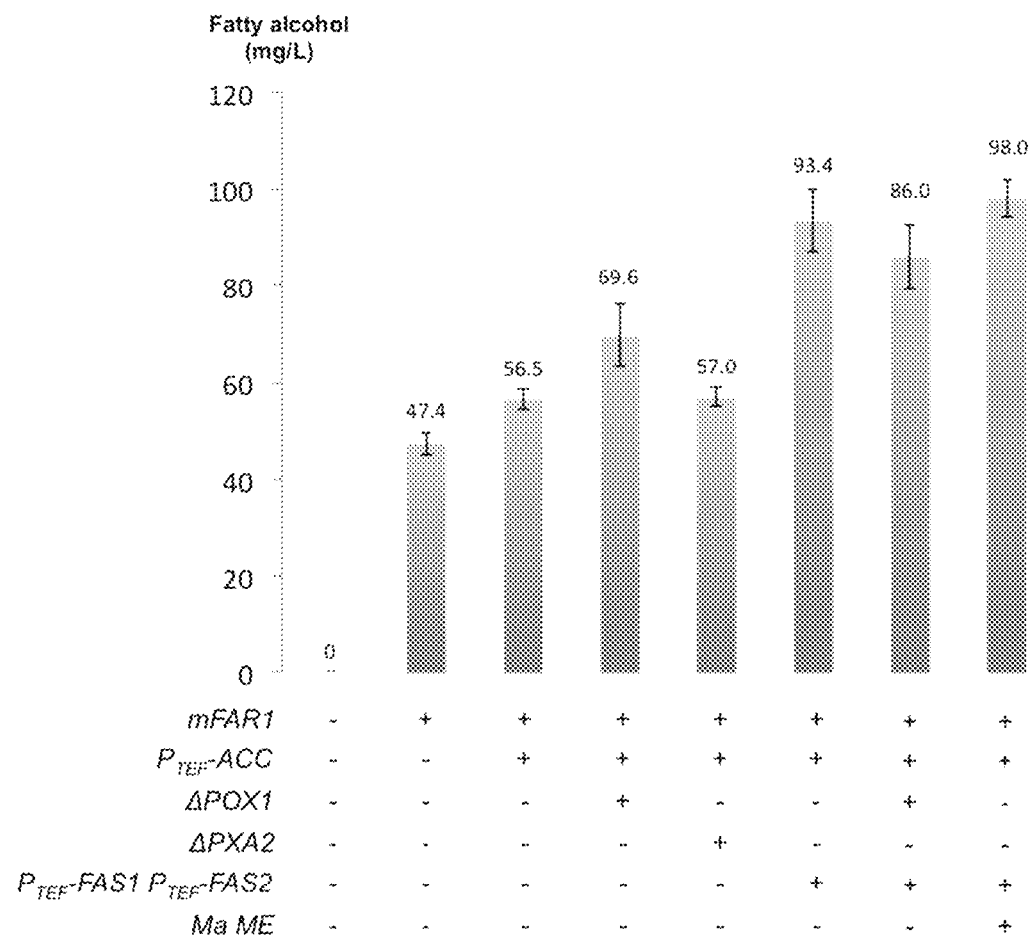
FIG. 3 shows fatty alcohol production in the mouse fatty acyl-CoA reductase-expressing and control strains. All strains were cultured in minimal medium lacking the appropriate amino acid and/or nucleotide and containing a mixed carbon source (0.2% glucose and 1.8% galactose). Values are the mean of three biological replicates±standard deviation (n=3) after 168 h.

In this study, we overexpressed mFAR1 in *S. cerevisiae*. Gratifyingly, our engineered strains produced and exported fatty alcohols into the medium, as demonstrated by the presence of fatty alcohols in the dodecane overlay (10% v/v). The empty vector control did not produce detectable levels of fatty alcohols. Plasmid-based overexpression of mFAR1 in BY4742 led to a fatty alcohol production of 47.4 mg/L (FIG. 3). Replacement of the native ACC1 promoter with $P_{Tef1}$ coupled to the plasmid-based overexpression of mFAR1 improved production levels to 56.5 mg/L. Finally, plasmid-based overexpression of mFAR1 in the WRY1 strain, which has all fatty acid biosynthesis genes driven by the strong constitutive promoter $P_{TEF1}$, improved production levels to 93.4 mg/L. Deletion of POX1, the first gene in the β-oxidation pathway, did not improve fatty alcohol production titer.

Given that the reduction of one molecule of fatty acyl-CoA to fatty alcohol requires one molecule of NADPH, we explored whether increasing the pool of cytosolic NADPH would lead to an increase in fatty alcohol yield. A common strategy to achieve this is by overexpressing an NADP-dependent malic enzyme (Moreira dos Santos et al., 2004; Wynn et al., 1999; Zhang et al., 2007). This oxidoreductase converts malate and NADP+ to pyruvate and NADPH, releasing one molecule of carbon dioxide in the process. We overexpressed the malic enzyme from the oleaginous fungus *Mortierella alpina* in our top fatty alcohol producer strain. This led to a small increase in the final fatty alcohol titer to 98.0 mg/L. The distribution of fatty alcohols was as follows: C16:0, 91.1% and C18:0, 8.9%. To the best of our knowledge, this is the highest production level of fatty alcohols reported in *S. cerevisiae*.

3.5.2 Overexpression of the Wax-Ester Synthase from *Acinetobacter calcoacericus* ADP1 (atfA) in *S. cerevisiae* LED to Production of Fatty Acid Ethyl Esters (FAEEs, Biodiesels)

Encouraged by our results in overproducing free fatty acids and fatty alcohols, we next turned our attention to fatty acid ethyl esters (biodiesels). Conversion of fatty acyl-CoAs into FAEEs requires an acyl-CoA:alcohol transferase (wax ester synthase, WS) that can accept ethanol, the most abundant short-chain alcohol in *S. cerevisiae*, as the alcohol substrate. Such an enzyme was recently identified from *Acinetobacter calcoaceticus* ADP1 (Stoveken et al., 2005). The enzyme, encoded by atfA, exhibits fatty acyl-CoA: alcohol acyltransferase activity towards a broad range of alcohol substrates including ethanol. Heterologously expressing this enzyme in *E. coli* (Steen, 2010), and more recently in *S. cerevisiae* CEN.PK, led to the production of FAEEs (Kalscheuer et al., 2004; Shi et al., 2012; Yu et al., 2012).

Figure 4:
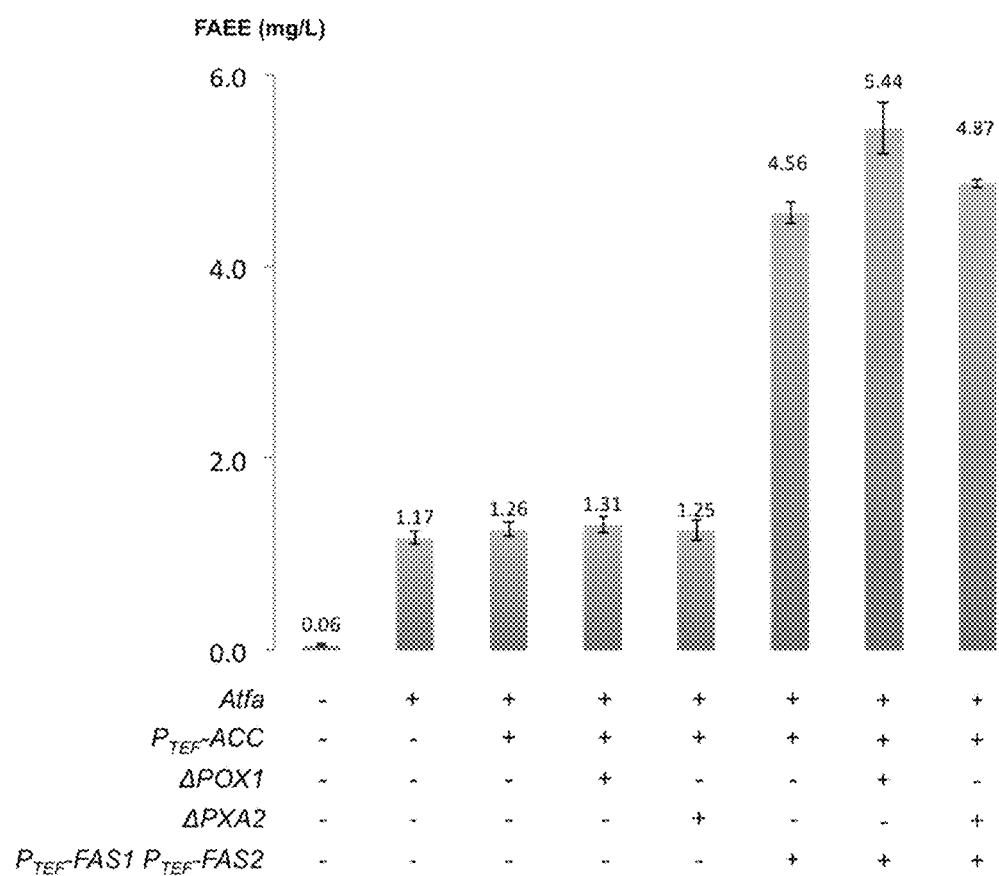
FIG. 4 shows fatty acid ethyl ester (FAEEs) production in the wax-ester synthase-expressing and control strains. All strains were cultured in minimal medium lacking the appropriate amino acid and/or nucleotide and containing a mixed carbon source (0.2% glucose and 1.8% galactose). Values are the mean of three biological replicates±standard deviation (n=3) after 168 h.

In this study, overexpression of the codon-optimized atfA led to the production of FAEEs, which were detected in the dodecane layer, suggesting that the compounds were produced and secreted into the medium. Plasmid-based expression of atfA in BY4742 led to FAEE production at 1.2 mg/L (FIG. 4). Replacement of the native ACC1 promoter with $P_{TEF1}$ coupled to the plasmid-based overexpression of atfA improved production levels to 1.3 mg/L. Finally, plasmid-based overexpression of atfA in the WRY1 strain, which has all fatty acid biosynthesis genes driven by the strong constitutive promoter $P_{TEF1}$, improved production levels to 4.6 mg/L. The production levels further improved slightly to 4.9 and 5.4 mg/L after the deletion of PXA2 and POX1, respectively. The latter is a 90-fold improvement over the level observed in the reference strain (empty vector control). The distribution of FAEEs was as follows: C12:0, 26.3%; C14:0, 14.9%; C16:0, 44.5%; and C18:0, 14.4%.

Intriguingly, the yield of FAEEs in our best producer is at least one order of magnitude lower than the yields of TAGs, free fatty acids and fatty alcohols in the corresponding best producers (~5 mg/L of FAEEs compared to about 400 mg/L of free fatty acids). We quantified ethanol levels in the culture medium to verify that ethanol production is not limiting. This was indeed the case as high levels of ethanol were observed in the culture medium (3.6 g/L after 72 hrs and 4.1 g/L after 168 hrs). Notably, the expression levels and in vivo activities of these enzymes in *S. cerevisiae*, the inherent toxicity of these fuel molecules, the ability of yeast to excrete these molecules into the medium could each contribute to differences in production titers. Understanding which of these factors plays the largest role in determining the yields of biofuel production will lead to further insights for metabolic engineering efforts.

4. CONCLUSIONS

Fatty acid-derived biofuels and chemicals are in great demand. Given the grave concerns over global climate change and the increasingly difficult access to fossil fuels, development of new microbial platforms for biofuel production is essential. Here, we engineered the budding yeast *S. cerevisiae* to produce fatty acid-derived biofuels and chemicals from simple sugars. Specifically, we overexpressed all three primary genes involved in fatty acid biosynthesis, namely ACC1, FAS1 and FAS2. Combining this metabolic engineering strategy with terminal "converting enzymes" (diacylglycerol-acyltransferase, fatty acyl-CoA thioesterase, fatty acyl-CoA reductase, and wax ester synthase for TAG, fatty acid, fatty alcohol and FAEE production, respectively) improved the production levels of all biofuel molecules and chemicals. In short, we demonstrated that *S. cerevisiae* provides a compelling platform for more scalable, controllable and economic route to this important class of chemicals.

While the present invention has been described with reference to the specific embodiments thereof, it should be understood by those skilled in the art that various changes may be made and equivalents may be substituted without

What is claimed is:

1. A genetically modified *Saccharomyces cerevisiae* host cell capable of producing one or more fatty acids, or fatty acid-derived compounds, or a mixture thereof, comprising:
   (a) increased expression of acetyl-CoA carboxylase, wherein the endogenous promoter of the ACC1 gene is replaced with promoter $P_{TEF1}$;
   (b) increased expression of one or more fatty acid synthases, wherein the endogenous promoter of the FAS1 and FAS2 genes are replaced with promoter $P_{TEF1}$;
   (c) optionally reduced expression of one or more enzymes in the β-oxidation pathway, wherein the endogenous POX1 and/or PXA2 genes are deleted;
   (d) a plasmid encoding an *Escherichia coli* TesA, which lacks a membrane signal peptide at a N-terminal end of TesA, operatively linked to promoter $P_{GAL10}$; and
   (e) reduced expression of fatty-acyl-CoA synthetases, wherein the endogenous FAA1 and/or FAA4 genes are deleted;
   wherein the host cell does not comprise the ΔSnf2 mutation and the host cell is capable of producing at least 162 mg of free fatty acids when cultured in one liter of culture medium.

2. The host cell of claim 1, wherein the one or more enzymes involved in or in the β-oxidation pathway are peroxisomal transporters PXA1 and PXA2, and β-oxidation enzymes PDX1, PDX2, and PDX3.

3. The host cell of claim 1, wherein the fatty acid-derived compound is a fatty acyl ethyl ester (FAEE), a fatty alcohol, a triacylglycerol (TAG), or a mixture thereof.

4. The host cell of claim 1, wherein the fatty acid is a C12:0, C14:0, C16:0, C16:1, C18:0, or C18:1, or mixture thereof, and the fatty acid-derived compound is a fatty acid methyl and ethyl esters (FAEE), fatty alcohol, or triacylglycerol (TAG) derived from one or more the following fatty acids: C12:0, C14:0, C16:0, C16:1, C18:0, and C18:1.

5. The host cell of claim 1, wherein the host cell is capable of producing at least 201 mg of free fatty acids when cultured in one liter of culture medium.

6. The host cell of claim 5, wherein the host cell is capable of producing at least 400 mg of free fatty acids when cultured in one liter of culture medium.

7. The host cell of claim 1, wherein the host cell comprises the following genotype: Mat α; his3Δ1; leu2Δ0; lys2Δ0; ura3Δ0.

8. A method of constructing a genetically modified *Saccharomyces cerevisiae* host cell of the claimed invention, comprising:
   (a) replacing the endogenous promoter of the ACC1 gene with promoter $P_{TEF1}$ and the endogenous promoter of the FAS1 and FAS2 genes with promoter $P_{TEF1}$;
   (b) optionally the deleting the endogenous POX1 and/or PXA2 genes;
   (c) introducing a plasmid encoding an *Escherichia coli* TesA, which lacks a membrane signal peptide at a N-terminal end of TesA, operatively linked to promoter $P_{GAL10}$ into the host cell;
   (d) deleting the endogenous FAA1 and/or FAA4 genes; and
   (e) culturing the host cell in a cell culture such that the cell culture produces at least 162 mg of free fatty acids per one liter of culture medium;
   wherein the host cell does not comprise the ΔSnf2 mutation.

9. The method of claim 8, wherein the host cell comprises the following genotype: Matα; his3Δ1; leu2Δ0; lys2Δ0; ura3Δ0.

10. A method of producing one or more fatty acids, or fatty acid-derived compounds, or a mixture thereof, in a genetically modified yeast host cell of claim 1, comprising culturing the genetically modified yeast host cell of claim 1 under a suitable condition such that the culturing results in the genetically modified yeast host cell producing the one or more fatty acids, or fatty acid-derived compounds, or a mixture thereof.

11. The method of claim 10, further comprising:
   recovering the one or more fatty acids, or fatty acid-derived compounds, or a mixture thereof, and optionally chemically treating the recovered compound to produce a second compound, wherein the second compound when combusted, can produce more energy that the combustion of the recovered compound.

* * * * *